US006472521B1

(12) United States Patent
Uhlmann et al.

(10) Patent No.: US 6,472,521 B1
(45) Date of Patent: Oct. 29, 2002

(54) OLIGONUCLEOTIDES FOR THE INHIBITION OF HUMAN EG5 EXPRESSION

(75) Inventors: Eugen Uhlmann, Glashütten; Beate Greiner, Bad Soden; Eberhard Unger; Gislinde Gothe, both of Jena-Cospeda; Marc Schwerdel, Jena, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/627,122

(22) Filed: Jul. 27, 2000

(30) Foreign Application Priority Data

Jul. 28, 1999 (DE) .......................................... 199 35 303

(51) Int. Cl.⁷ ..................... C07H 21/04; C07H 21/00; C12Q 1/68

(52) U.S. Cl. ................... 536/24.5; 435/6; 435/375; 435/377; 435/455; 536/23.1; 536/24.1; 536/25.3; 514/44

(58) Field of Search ........................... 436/6, 375, 377, 436/455; 536/23.1, 24.1, 24.5, 25.3; 514/44

(56) References Cited

U.S. PATENT DOCUMENTS

| | | | |
|---|---|---|---|
| 5,750,669 A | 5/1998 | Rösch et al. | |
| 5,789,562 A | 8/1998 | Seela et al. | |
| 5,801,154 A | * 9/1998 | Baracchini et al. | ............ 514/44 |
| 5,844,106 A | 12/1998 | Seela et al. | |
| 5,874,553 A | 2/1999 | Peyman et al. | |
| 6,013,639 A | 1/2000 | Peyman et al. | ................ 514/44 |
| 6,028,182 A | 2/2000 | Uhlmann et al. | |
| 6,033,909 A | 3/2000 | Uhlmann et al. | |
| 6,066,720 A | 5/2000 | Seela et al. | |

FOREIGN PATENT DOCUMENTS

| | | | |
|---|---|---|---|
| EP | 0 171 066 | 2/1986 | |
| EP | 0 552 766 A2 | 7/1993 | |
| EP | 0 653 439 A2 | 5/1995 | |
| EP | 0 672 677 A2 | 9/1995 | |
| EP | 0 680 969 A2 | 11/1995 | |
| EP | 0 710 667 A2 | 5/1996 | |
| EP | 0 726 274 A2 | 8/1996 | ........... C07H/21/00 |
| EP | 0 739 898 A2 | 10/1996 | |
| EP | 0 464 638 B1 | 4/1997 | |
| EP | 0 593901 B1 | 4/1997 | |
| WO | WO 95/01363 | 1/1995 | |

OTHER PUBLICATIONS

W James Antiviral Chemistry & Chemotherapy, "Towards gene–inhibition therapy:a review of progress and prospects in the field of antiviral antisense acids nucleic and ribozymes," 1991, 2(4), pp. 191–214.*
Eugen Uhlmann, et al., "Antisense Oligonucleotides: A New Therapeutic Principle," Chemical Reviews, vol. 90, No. 4, pp. 543–584 (1990).

Sudhir Agrawal, "Antisense oligonucleotides: towards clinical trials," Tibtech, vol. 14, pp. 376–387 (1996).
Louis J. Ravin, "Preformulation" from Chap. 76 in *Remington's Pharmaceutical Science*, 17th Ed., (Alfonso Gennaro, ed.) pp. 1409–1423, 1418 (1985).
Narendra K. Vaish, et al., "Recent developments in the hammerhead ribozyme field," Nucleic Acids Research, vol. 26, No. 23, pp. 5237–5242 (1998).
Stanlay T. Crooke, et al., "Progress in Antisense Oligonucleotide Therapeutics," Annu. Rev. Pharmacol. Toxicol, vol. 36, pp. 107–129 (1996).
Jürg Hunziker, et al., "Nucleic Acid Analogues: Synthesis and Properties," in *Modern Synthetic Methods*, vol. 7, Chapter 2, (Beat Ernst and Christian Lumann, eds.) Verlag Helvetica Chimica Acta, Basel, (1995).
Eugene P. Stirchak, et al., "Uncharged stereoregular nucleic acid analogs: 2. Morpholino nucleoside oligomers with carbamate internucleoside linkages," Nucleic Acids Research, vol. 17, No. 15, pp. 6129–6141 (1989).
Peter E. Nielsen, et al., "Peptide Nucleic Acid (PNA). A DNA Mimic with a Peptide Backbone," Bioconjugate Chem. vol. 5, pp. 3–7 (1994).
Anusch Peyman, et al., "Phosphonic Ester Nucleic Acids (PHONAs): Oligonucleotide Analogues with an Archiral Phosphonic Acid Ester Backbone," Angew. Chem. Int. Ed. Engl., vol. 35, No. 22, pp. 2636–2638 (1996).
Brian C. Froehler, et al., "Triple–Helix Formation by Oligodeoxynucleotides Containing the Carbocyclic Analogs of Thymidine and 5–Methyl–2'–deoxycytidine," J. Am. Chem. Soc., vol. 114, pp. 8320–8322 (1992).
Frank Vandendriessche, et al., "Acyclic Oligonucleotides: Possibilities and Limitations," Tetrahedron, vol. 49, No. 33, pp. 7223–7238 (1993).
Markus Tarköy, et al., Nucleic–Acid Analogues with Constraint Conformational Flexibility in the Sugar–Phosphate Backbone ('Bicyclo–DNA'), Helvetica Chimica Acta, vol. 76, pp. 481–510 (1993).
Muthiah Manoharan, "Designer Antisense Oligonucleotides: Conjugation Chemistry and Functionality Placement," Chapter 17, *Antisense Research and Applications*, (Crooke & Lebleu, eds.), CRC Press, Boca Raton, pp. 303–349 (1993).
Masakazu Koga, et al., "Alternating α,β–Oligothymidylates with Alternating (3'→3')– and (5'→5')–Internucleotidic Phosphodiester Linkages as Models for Antisense Oligodeoxyribonucleotides," Journal of Organic Chemistry, vol. 56, No. 12, pp. 3757–3763 (1991).

(List continued on next page.)

*Primary Examiner*—Sean McGarry
(74) *Attorney, Agent, or Firm*—Finnegan, Henderson, Farabow, Garrett, & Dunner, L.L.P.

(57) ABSTRACT

The present invention relates to an oligonucleotide or a derivative thereof which has a sequence that corresponds to a particular fragment of a nucleic acid sequence which encodes human eg5 or a mutant form thereof; the invention further relates to a method of making the oligonucleotide and the use thereof.

12 Claims, 1 Drawing Sheet

OTHER PUBLICATIONS

Anusch Peyman, et al., "Minimally Modified Oligonucleoties—Combination of End–Capping and Pyrimidine–Protection," Bio. Chem. Hoppe–Seyler, vol. 377, pp. 67–70 (1996).

C.A. Stein, et al., "Problems in interpretation of Data Derived from in Vitro and in Vivo Use of Antisense Oligodeoxynucleotides" Antisense Research and Development, vol. 4, pp. 67–69 (1994).

Paul F. Torrence, et al., "Targeting RNA for degradation with a (2'5')oligoadenylate–antisense chimera," Proc. Natl. Acad. Sci. USA, vol. 90, pp. 1300–1304 (1993).

L. J. McBride, et al., "An Investigation of Several Deoxynucleoside Phosphoramidites Useful for Synthesizing Deoxyoligonucleotides," Tetrahedron Letters, vol. 24, No. 3, pp. 245–248 (1983).

E. Sonveaux, "The Organic Chemistry Underlying DNA Synthesis," Bioorganic Chemistry, vol. 14, pp–274–325 (1986).

Norman Weiner, et al., "Liposomes as a Drug Delivery System," Drug Development and Industrial Pharmacy, vol. 15, No. 10, pp. 1523–1554 (1989).

E. Uhlmann, et al., "Chemical 5–'–Phosphorylation of Oligonucleoties Valuable in Automated DNA Synthesis," Tetrahedron Letters, vol. 27, No. 9, pp. 1023–1026 (1986).

Anne Blangy, et al., "Phosphorylation by p34$^{cdc2}$ Regulates Spindle Association of Human Eg5, a Kinesin–Related Motor Essential for Bipolar Spindle Formation In Vivo," Cell, vol. 83, pp. 1159–1169 (1995).

Astrid Kaiser, et al., "All–trans–Retinoic Acid–mediated Growth Inhibition Involves Inhibition of Human Kinesin––related Protein HsEg5" J. Biol. Chem., 274(27):18925–31 (1999).

Anusch Peyman and Eugen Uhlmann, "Minimally Modified Oligonucelotides—Combination of End–Capping and Pyrimidine–Protection" Biol. Chem., 377:67–70 (1996).

Claire E. Walczak, et al. "A Model for the Proposed Roles of Different Microtubule–based Motor Proteins in Establishing Spindle Bipolarity" Curr. Biol., 8(16):903–13 (1998).

\* cited by examiner

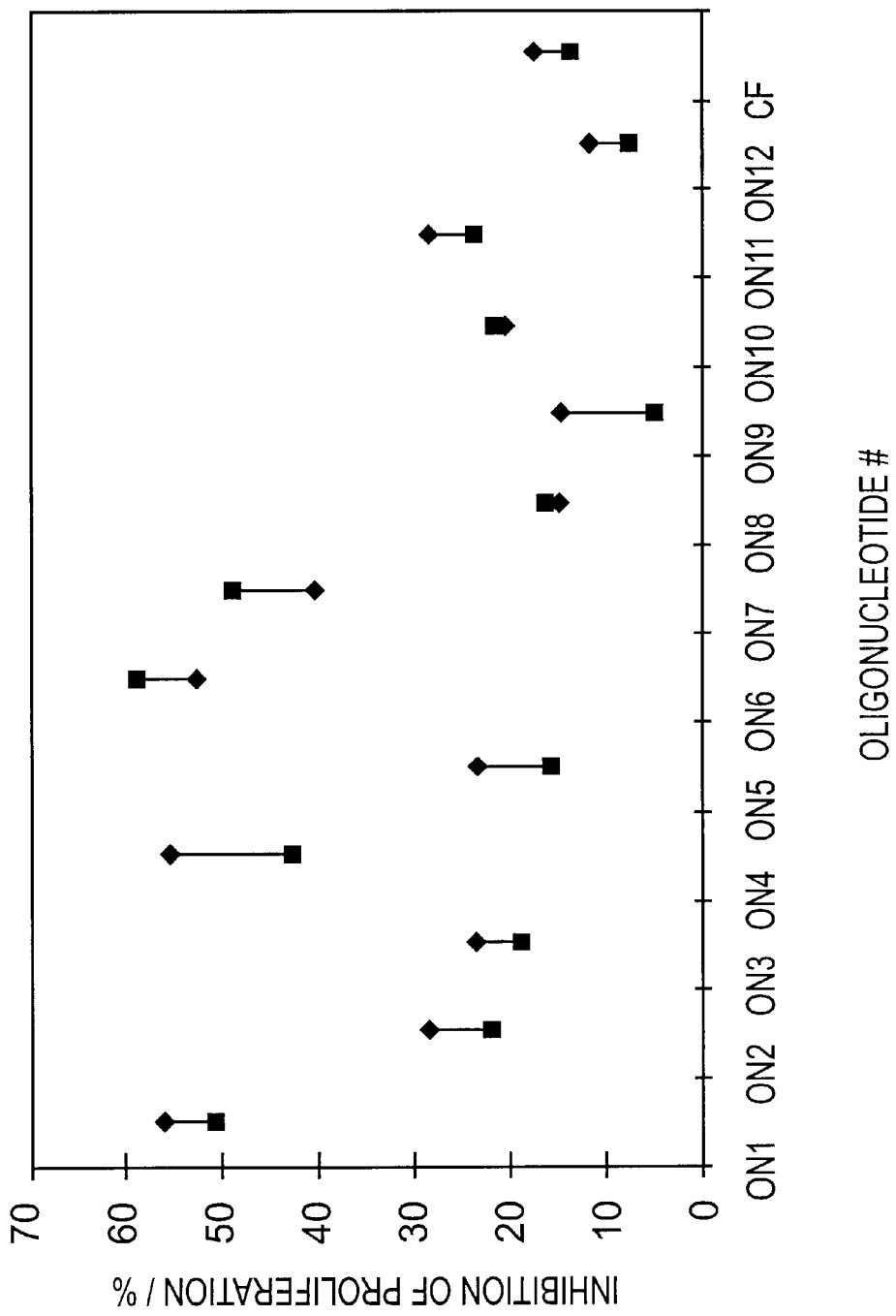

SEQUENCE LISTING

<160> NUMBER OF SEQ ID NOS: 23

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
cgacgccatg acggaattc                                                19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
aatggtctgc atctcacca                                                19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
ggctgcgacg ccatgacgg                                                19

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
atgacggaat tc                                                       12

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
ccatgacgga at                                                       12

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
acgccatgac gg                                                           12

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
gcgacgccat ga                                                           12

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
ggctgcgacg cc                                                           12

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
ttggctgcga cg                                                           12

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
cgacgccatg acggaattc                                                    19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
aatggtctgc atctcacca                                                    19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
ggctgcgacg ccatgacgg                                               19

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
atgacggaat tc                                                      12

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
ccatgacgga at                                                      12

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
acgccatgac gg                                                      12

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
gcgacgccat ga                                                      12

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
ggctgcgacg cc                                                      12

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
ttggctgcga cg                                                      12

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: oligonucleotide

<400> SEQUENCE: 19
cggatcctct cactgagaa                                                     19

<210> SEQ ID NO 20
<211> LENGTH: 3741
<212> TYPE: DNA
<213> ORGANISM: Homo sapiens

<400> SEQUENCE: 20
gaattccgtc atggcgtcgc agccaaattc gtctgcgaag aagaaagagg agaagggaa         60 gaacatccag gtggtggtga gatgcagacc atttaatttg gcagagcgga aagctagcgc       120
ccattcaata gtagaatgtg atcctgtacg aaaagaagtt agtgtacgaa ctggaggatt       180
ggctgacaag agctcaagga aaacatacac ttttgatatg gtgtttggag catctactaa       240
acagattgat gtttaccgaa gtgttgtttg tccaattctg gatgaagtta ttatgggcta       300
taattgcact atctttgcgt atggccaaac tggcactgga aaaactttta caatggaagg       360
tgaaaggtca cctaatgaag agtataccig ggaagaggat cccttggctg gtataattcc       420 acgtacccti catcaaattt ttgagaaact tactgataat ggtactgaat tttcagtcaa       480
agtgtctctg ttggagatct ataatgaaga gcttttttgat cttcttaatc catcatctga       540
tgtttctgag agactacaga tgtttgatga tccccgtaac aagagaggag tgataattaa       600
aggtttagaa gaaattacag tacacaacaa ggatgaagtc tatcaaattt tagaaaaggg       660
ggcagcaaaa aggacaactg cagctactct gatgaatgca tactctagtc gttcccactc       720
agttttctct gttacaatac atatgaaaga actacgatt gatggagaag agcttgttaa       780
aatcggaaag ttgaacttgg ttgatcttgc aggaagtgaa acattggcc gttctggagc       840 tgttgataag agagctcggg aagctggaaa tataaatcaa tccctgttga ctttgggaag       900
ggtcattact gcccttgtag aaagaacacc tcatgttcct tatcgagaat ctaaactaac       960
tagaatcctc caggattctc ttgggggcg tacaagaaca tctataattg caacaattc      1020 tcctgcatct ctcaatcttg aggaaactct gagtacattg gaatatgctc atagagcaaa      1080
gaacatattg aataagcctg aagtgaatca gaaactcacc aaaaaagctc ttattaagga      1140
gtatacggag gagatagaac gtttaaaacg agatcttgct gcagcccgtg agaaaaatgg      1200
agtgtatatt tctgaagaaa attttagagt catgagtgga aaattaactg ttcaagaaga      1260
gcagattgta gaattgattg aaaaaattgg tgctgttgag gaggagctga ataggttac      1320 agagttgttt atggataata aaatgaact tgaccagtgt aaatctgacc tgcaaaataa      1380
aacacaagaa cttgaaacca ctcaaaaaca tttgcaagaa actaaattac aacttgttaa      1440
agaagaatat atcacatcag ctttggaaag tactgaggaa aaacttcatg atgctgccag      1500
caagctgctt aacacagttg aagaaactac aaaagatgta tctggtctcc attccaaact      1560
ggatcgtaag aaggcagttg accaacacaa tgcagaagct caggatattt ttggcaaaaa      1620
cctgaatagt ctgtttaata atatggaaga attaattaag gatggcagct caaagcaaaa      1680
ggccatgcta gaagtacata agaccttatt tggtaatctg ctgtcttcca gtgtctctgc      1740

```
attagatacc attactacag tagcacttgg atctctcaca tctattccag aaaatgtgtc    1800
tactcatgtt tctcagattt ttaatatgat actaaaagaa caatcattag cagcagaaag    1860
taaaactgta ctacaggaat tgattaatgt actcaagact gatcttctaa gttcactgga    1920
aatgatttta tccccaactg tggtgtctat actgaaaatc aatagtcaac taaagcatat    1980
tttcaagact tcattgacag tggccgataa gatagaagat caaaaaaaaa ggaactcaga    2040
tggctttctc agtatactgt gtaacaatct acatgaacta caagaaaata ccatttgttc    2100
cttggttgag tcacaaaagc aatgtggaaa cctaactgaa gacctgaaga caataaagca    2160
gacccattcc caggaacttt gcaagttaat gaatctttgg acagagagat tctgtgcttt    2220
ggaggaaaag tgtgaaaata tacagaaacc acttagtagt gtccaggaaa atatacagca    2280
gaaatctaag gatatagtca acaaaatgac ttttcacagt caaaaatttt gtgctgattc    2340
tgatggcttc tcacaggaac tcagaaattt taaccaagaa ggtacaaaat tggttgaaga    2400
atctgtgaaa cactctgata aactcaatgg caacctggaa aaaatatctc aagagactga    2460
acagagatgt gaatctctga acacaagaac agtttatttt tctgaacagt gggtatcttc    2520
cttaaatgaa agggaacagg aacttcacaa cttattggag gttgtaagcc aatgttgtga    2580
ggcttcaagt tcagacatca ctgagaaatc agatggacga aaggcagctc atgagaaaca    2640
gcataacatt tttcttgatc agatgactat tgatgaagat aaattgatag cacaaaatct    2700
agaacttaat gaaaccataa aaattggttt gactaagctt aattgctttc tggaacagga    2760
tctgaaactg gatatcccaa caggtacgac accacagagg aaaagttatt tatacccatc    2820
aacactggta agaactgaac cacgtgaaca tctccttgat cagctgaaaa ggaaacagcc    2880
tgagctgtta atgatgctaa actgttcaga aaacaacaaa gaagagacaa ttccggatgt    2940
ggatgtagaa gaggcagttc tggggcagta tactgaagaa cctctaagtc aagagccatc    3000
tgtagatgct ggtgtggatt gttcatcaat tggcggggtt ccattttcc agcataaaaa     3060 atcacatgga aaagacaaag aaaacagagg cattaacaca ctggagaggt ctaaagtgga    3120
agaaactaca gagcacttgg ttacaaagag cagattacct ctgcgagccc agatcaacct    3180
ttaattcact tgggggttgg caattttatt tttaaagaaa aacttaaaaa taaaacctga    3240
aaccccagaa cttgagcctt tgtgtatagat tttaaagaa tatatatatc agccgggcgc    3300
gtggctctag ctgtaatccc agctaacttt ggaggctgag gcgggtggat tgcttgagcc    3360
caggagtttg agaccagcct ggccaacgtg cgctaaaacc ttcgtctctg ttaaaaatta    3420
gccgggcgtg gtgggcacac tcctgtaatc ccagctactg gggaggctga ggcacgagaa    3480
tcacttgaac ccagaagcgg ggttgcagtg agccaaaggt acaccactac actccagcct    3540
gggcaacaga gcaagactcg gtctcaaaaa taaaatttaa aaaagatata aggcagtact    3600
gtaaattcag ttgaattttg atatctaccc attttctgt catccctata gttcactttg     3660
tattaaattg ggtttcattt gggatttgca atgtaaatac gtatttctag ttttcatata    3720
aagtagttct tttaggaatt c                                             3741

<210> SEQ ID NO 21
<211> LENGTH: 5340
<212> TYPE: DNA
<213> ORGANISM: Plasmodium falciparum

<400> SEQUENCE: 21
tttttttttt ttattccttt ggatgttctt ggtagtttaa attttttatt tttgtagttt     60
```

-continued

```
tcttctttta tacgtttttaa agcaggggat gccttttag gaaatgccct attttcaata      120
gctttaattt ttgtagattg aaatttatta ttattattat tattattgtt gttgttgttg      180
ttgttgttgt tgttgttatt atttgaataa ttatttgtta tatgaacatt ttgaacattt      240
atatttctct ttctttcata ttcttttaaa cttgttacac tcatattttc tgtatttaca      300
tcaaatcttt tattatgttg attgttattt aaataattta attcttgata tgtttcatct      360
attggttgta taggattatc cgttgtattc ttattatata gcatatattc atttaagggt      420
agattattgt gattagtttt tacatttaat ttattttat cacctttatt atttatatta       480
tgaggtatac tactattcgt tgtatgatca tttaaactat tgtaacgaga gtaattattt      540
tcatgcgcta caattttatc atcttgaata agaaattgga agttttcatc gatttgttca      600
aatactttac ttaaatctat atcatgtgtt gttgtaattt gttctatctc tttcatcaag      660
gtattttaa cttccaagta taaattttgt cttatgatat catcattata aagataataa       720
ttatgatgat caccttgatc tatttatta tcatcattat aaagataata attatgatga       780
tcaccttgat ccattttatt atcatcatta taaagataat tattatgatc atgaccttga      840
tccatttat tatcatcatt ataaagataa ttattatgat catgaccttg atccatttta       900
ttatcatcat tataaagata attattatga tcatgacctt gatccatttt attatcatca      960
taattattat tgtcaccatt tttattattg tcatgatcat ttttattatt gtcaccattt     1020
ttattattat catgattatt tttattatta tcatgattat ttttattatt atcatgatta     1080
ttttattat tatcatcatt tttattatta tcataattcg tgtcgtaagt cgaatcccta      1140
tttagtgatg tgattttcat cggagtaaac atatctatga cattcacaaa cgtttcccett    1200
atcctttgta catcatcctt tatatttaga taaaattcat catccatatt ttccatgaga     1260
tcataacttg atgtacttgg aatgtcttgt aagtaatctt tttttttaa tatatctatt      1320
aattctgcta tatacatatt acatttgttt aaattttgtt caaatatatt attaaaaagt     1380
tttatatttt cattagactt taacatatgt atacgacgtc ccccttttg ttcttgtgat      1440
tctttatttt tattttgtaa aatcttttca gatataacgt tatataactt tcgtttctct     1500
attttgttta tattagtttg acttgtaaag ttatttatga ttttatcaat atttagatta     1560
tttgtatata ataaattatt ataaatattt aagtatcat ttaaacattt gctgtgttcc      1620
ttttcttcaa tataactttt tcttttaaa taagataata tgttatataa aacagtatga      1680
taatttgtta tcttcctttt aatatcatta ttaatattat tatattcctt ttcatcatta     1740
atattgcatt cagaaaaatg ttgtatagta tcatctatct tttttacaga attcataaaa     1800
acagatttat aatttttttt tgacttatca tataattctt tatttaataa atcgaacttg     1860
ttattcattt tttcataaat atcttccaca ttttatttta taagtaattc aatatctttc     1920
aaaatatttc ctttaaattc ttgtatatct tcatttatca ttttttata attattaatt     1980
ataatattat cctccttttc aaaaacatca tattttttat aaatatattc aatgttgtca     2040
ttcataatct tcttgtcctt atcccaatgt atatatttt catgacattt ttttctagt       2100
aacataaatg attcgtttaa aaaaatatga aatatattac atatactttt aatatattgt     2160
attaatgatt ttgcattata taactttttt tcagattcgt gattatctaa attttgtata     2220
atatcttcac cttgtctatt taataataaa tcttttataa attctttatt ctcaggataa     2280
ttaaatgatt cctctatatg gtcaaatggc atctccattat tttcttcttt accatattgt     2340
ttttgacatg ttttccttc accattttgt ttttcacata ttattccttc accgttttgt      2400
ttttcacata ttatctcgtc accgttttgt ttttcacata ttatctttc accactttgt      2460
```

```
ttttcacata ttatctcttc accgttttgt ttttcacata ttatcttttc accactttgt   2520
ttttcacata ttatcttttc accactttgt ttttcacata ttatcttttc accactttgt   2580 ttttctttttt ttaatccgtt tgtattatat acaccaataa ttgctggcat tttctgcttg   2640
gcttcatcac ttatatgtgg tatgtttatt ttacattgtg atatttcctt tttaatattt   2700
tcggagagag aaaagtaatc atgatcatat ttttgtaaaa tatccatatg gtccagtata   2760
aaattcagag tatcattata tttaaaatta atgttactat tgagttcttc aaaatggtta   2820
atataatcat tgtatgattt tttattttgt actagataat ttttggtatc atctaaaatg   2880
aataagatgg ttttacatat atcgtttaaa agatgatttt cttgatgaat attttttttt   2940
atatttaata gattatcatg cattatatta gacatatttg ttttaatttg ttgaaaagat   3000 ttttttttgat ttataaaatt ttcttctaaa gaatgatatt tatttaataa gaattgtgta   3060 atatatttt cttctattat ttttttaatt aatatttgat gaaatgcttg tatattttta   3120 tattttgaa tagtatcttt taaaagaaa atatttttat tttgtagatc atctgtatta   3180
tccattttat ttaataaatt ttttatttttt ttacttttttt caaataaaat ttttttctttt   3240 tctaataata tttctttatt tttctttaga ctattttgta tattattata ttcttctgta   3300
tcaagataaa caccctctctt ttctctgctt aaattcagtg catttcttaa cttttcgatt   3360
tcattattta aatcctttat ttttaattgt ttcgttgttt ttatatttat ctcgggtcta   3420
ttcttaatat tcttagctcg aaagacataa tctaaagtgc ttaaagtctc atcaatacat   3480
aaagaggagg gtgatatagt ggcgacaata aaagtcttcg ttttcccacc taacgaatct   3540
tgtaataatc tggttaattt agaatctctg taaggaatat aagatgaatt ctcaatcaac   3600
gaattaataa ctctacctaa ggttaataaa gattgattta tattacaact ttcttgttgt   3660 ctaatttta aagaaccata agagcttttc aaagcatttt cactacccgc taaatcaact   3720
aaatttaatt ttcctatttt tgttatactt tctcctacat tatttatatc ttttataatt   3780
aatgttatag taaaaatcga atgacttcta ctcgattttt tattataagc cgtttcagct   3840
gtccttcttt ttttaatagc tgaacatata atataatata tttcttcaaa agaattaata   3900
cttttttctt ctaacttatc aacatttaat cctttacttt tattattact atcttcatat   3960
attcgaagtt tcatattttc atttgttgaa cttaataaat cacataattc ttcattatat   4020
atttctagat agctaatttt tatattaaaa tcgtacatat tcttatcatc aaatgtttga   4080
tacatatcat tattcctatt tttatctaca ctacattttt gtacaacatc acaagtaata   4140
tctctactct tttcgttaac taacaaattg ttaggttctt tattaatttt taaattatta   4200
taaatatcat ttttatcaat atttattttg ttacataata aattattata attattatta   4260
ataatattat tattgttacc attagtttcc ttatttatta catttatatg ttcgttatcc   4320
ttttcatcaa atatattctt ttttccttta aaatgtcgaa tctttctcttc tttccttta   4380 tttaatatat cgaatattct tttcgtaact cgaaatataa gtccagtatc ctcattctca   4440
caaagttcat agcaatagct gatgtcgcta ttaatacttt cattcaaatc caccttttta   4500
ttattatcat attgtttcag gtgttctagt attttccctt ccatagtata ggtcttaccc   4560
gtcccggtct gtccatagca gaacagcgta caattgaatc cttgcaaaac ctgaagcggc   4620
gaacaaaaaa aaaaaaaaaa aaaatatat atatatatgt acatgtatat ttatatgtat   4680
atgtatatat atatgtatag ttatatgtat ttttattttt attttatttt ttatatttat   4740
ttttattttt atatttattt ttattttttat atttattttt atttttatat ttatatttat   4800
```

```
atatgtgtaa aattaacatg gggagcaaag aatttcccat atatttttt ttttaatct    4860 atttaataaa acattattat gatatacgca gaggtgatat atacatggta tttatttatt   4920 ttttttata tattttcat ttgtttcgta ggaatattct tttttttct gcacatatat    4980 ttcactatcc atataatatc ataatacatc atggaataat ttatatatat atatatatat   5040
atgtatattt tattttacc tcatctacta tttggtaaat ataattattg aacaaagttt   5100
tctgatccac atctttatca catgcataat caaaactata ttttttttcg tatatttcat   5160
tgtttctatt aattgttaat ataacctcat tattattaat tcgaactacc tcttcattat   5220
ttatatcgtt tttttcttt tcatttaatg gtctacacct tacgataact tttatattta   5280
cgcaacttga tttatcatta ttataagaat ttctgagcat tttactttta ttcaaataat   5340
```

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: oligonucleotide

<400> SEQUENCE: 22
gcgacgccat gacgg                                                    15

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: oligonucleotide

<400> SEQUENCE: 23
cgacgccatg ac                                                       12

OLIGONUCLEOTIDES FOR THE INHIBITION OF HUMAN EG5 EXPRESSION

FIELD OF THE INVENTION

The present invention relates to an oligonucleotide or a derivative thereof corresponding to a particular fragment of a nucleic acid sequence encoding a human eg5 or a mutant form thereof. The invention further relates to a method of making the oligonucleotide and the use thereof.

BACKGROUND OF THE INVENTION

During mitosis a microtubule-based spindle apparatus helps distribute the duplicated chromosomes equally to the daughter cells. Kinesin-related motor proteins are part of the forces required for spindle assembly and chromosome segregation. The formation of a bipolar mitotic spindle involves the activity of many different motor proteins. One human kinesin-related motor protein is human eg5, which interacts with the mitotic centrosomes and has been shown to be essential for bipolar spindle formation (Blangy et al., Cell (1995)83, 1159). Microinjection of specific anti-human-eg5 antibodies blocks centrosome migration and causes cells to arrest in mitosis.

Another method for blocking bipolar spindle formation is the inhibition of eg5 expression. One way to specifically inhibit eg5 expression is by the use of antisense oligonucleotides, which can be optionally modified in order to improve their properties (E. Uhlmann and A. Peyman, *Chemical Reviews* 90:543 (1990); S. Agrawal, *TIBTECH* 1996:376). Antisense oligonucleotides are thought to bind to specific sequences of the mRNA, resulting in degradation of the mRNA and/or inhibition of protein synthesis.

SUMMARY OF THE INVENTION

The present invention provides an oligonucleotide or a derivative thereof corresponding to a fragment of the nucleic acid sequence encoding an eg5 gene—preferably, human eg5 or a pathogenic organism's eg5, e.g., *Plasmodium falciparum* (malaria). For example, the oligonucleotide comprises from 8 to about 100 nucleotides, preferably from about 8 to about 20 nucleotides of the eg5 sequence. The oligonucleotide or derivative thereof binds to the nucleic acid sequence of eg5 and inhibits the formation of the eg5 protein. The human eg5 nucleic acid sequence has been reported (Blangy et al., *Cell* 83:1159 (1995)). SEQ ID NO.: 20 is an example of a nucleic acid sequence that encodes human eg5. SEQ ID NO.: 21 is an example of a *Plasmodium falciparum* eg 5 nucleic acid sequence.

BRIEF DESCRIPTION OF THE FIGURE

FIG. 1 summarizes the results of Examples 1+2. The effect of oligonucleotides ON1 to ON12 (eg5 antisense) on the inhibition of proliferation of REH cells (in percent) is shown.

DETAILED DESCRIPTION OF THE INVENTION

Preferably, the oligonucleotide has a sequence that corresponds to a fragment of a nucleic acid that encodes human eg5 or *Plasmodium falciparum* eg5. The phrase "corresponds to" means that the base sequence of the oligonucleotide is complementary to a part of a nucleic acid sequence that encodes eg5 (e.g., gene, cDNA, mRNA), and therefore, allows the oligonucleotide to hybridize to or bind to the sense strand of the nucleic acid encoding the eg5 protein. This is why it is called an "antisense oligonucleotide". Therefore, in a preferred embodiment of the invention, the oligonucleotide is an antisense oligonucleotide.

In another preferred embodiment of the invention, the oligonucleotide is a ribozyme. A ribozyme is a catalytic nucleic acid that cleaves mRNA. Preferably, the ribozyme is selected from the group of hammerhead ribozymes (Vaish et al., *Nucleic Acids Res.* (1998) 26:5237).

An oligonucleotide according to the invention binds to a part of the eg5 mRNA, which is appropriate for hybridization and inhibits formation of the eg5 protein. Oligonucleotides which are appropriate for binding to eg5 mRNA and inhibit expression are, e.g., oligonucleotides directed against the translational starter region of eg5. The part of the eg5 encoding nucleic acid sequence corresponding to the oligonucleotide corresponds to a length of 8, 9, 10, 11, 12, 13, 14, 15, 16, 17, 18, 19, 20 or more nucleotides, and, preferably, the oligonucleotide corresponds to a length of 12 nucleotides or 19 nucleotides of an eg5 encoding sequence. Therefore, an oligonucleotide according to the invention has a length of 10 (10mer), 11 (11 mer), 12 (12mer), 13 (13mer), 14 (14mer), 15 (15mer), 16 (16mer), 17 (17mer), 18 (18mer) or 19 (19mer) nucleotides.

In a preferred embodiment of the invention, the oligonucleotide has a length of 12 or 19 nucleotides; such oligonucleotides might for example, have one of the following sequences: SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, or a fragment thereof, wherein

SEQ ID NO. 1: 3-'CTTMGGCAGTACCGCAGC-5';
  5'CGACGCCATGACGGAATTC-3'

SEQ ID NO. 2: 3'-ACCACTCTACGTCTGGTAA-5';
  5'-MTGGTCTGCATCTCACCA-3'

SEQ ID NO. 3: 3'-GGCAGTACCGCAGCGTCGG-5';
  5'-GGCTGCGACGCCATGACGG-3'

SEQ ID NO. 4: 3'-CTTAAGGCAGTA-5';
  5'-ATGACGGAATTC-3'

SEQ ID NO. 5: 3'-TAAGGCAGTACC-5';
  5'-CCATGACGGMT-3'

SEQ ID NO. 6: 3'-GGCAGTACCGCA-5';
  5'-ACGCCATGACGG-3'

SEQ ID NO. 7: 3'-AGTACCGCAGCG-5';
  5'-GCGACGCCATGA-3'

SEQ ID NO. 8: 3'-CCGCAGCGTCGG-5';
  5'-GGCTGCGACGCC-3'

SEQ ID NO. 9: 3'-GCAGCGTCGGTT-5';
  5'-TTGGCTGCGACG-3'.

Very particularly preferably, the oligonucleotide is modified in order to improve its properties, e.g., to increase its resistance to nucleases or to make it resistant to nucleases, to improve its binding affinity to a complementary eg5 encoding nucleic acid, e.g., mRNA, or to increase its cellular uptake.

Therefore, the present invention preferably relates to an oligonucleotide that has a particular sequence as outlined above and that has, in addition, one or more chemical modifications in comparison to a "natural" DNA, which is composed of the "natural" nucleosides deoxyadenosine (adenine+β-D-2'-deoxyribose), deoxyguanosine (guanine+β-D-2'-deoxyribose), deoxycytidine (cytosine+β-D-2'-deoxyribose), and thymidine (thymine+β-D-2'-deoxyribose) linked via phosphodiester internucleoside bridges. The oligonucleotides can have one or more modifications of the same type and/or modifications of a different type; each type of modification can be independently selected from the other types of modifications known to be used for modifying oligonucleotides.

The invention also relates to derivatives of the oligonucleotides, for example, their salts, in particular their physiologically tolerated salts. Salts and physiologically tolerated salts are, e.g., described in Remington's Pharmaceuticals Science (1985) Mack Publishing Company, Easton, PA (page 1418). Derivatives also relate to modified oligonucleotides that have one or more modifications. These modifications may be at particular nucleotide positions and/or at particular internucleoside bridges, or the oligonucleotide may be an analog (e.g., polyamide-nucleic acids (PNAs), phosphomonoester nucleic acids (PHONAs= PMENAs). The oligonucleotide may also be a chimera, e.g., a chimera composed of a DNA and a PNA part or composed of a DNA and a PHONA part. Derivatives also relate to oligonucleotides that correspond to alleles and/or mutant forms of a normal or natural eg5, e.g., alleles and/or mutants of human eg5, e.g., SEQ ID NO. 20, and alleles and/or mutants of *Plasmodium falciparum* eg5, e.g., SEQ ID NO. 21.

Examples of chemical modifications are known to the skilled person and are described, for example, in E. Uhlmann and A. Peyman, *Chemical Reviews* 90:543 (1990); "Protocols for Oligonucleotides and Analogs" *Synthesis and Properties & Synthesis and Analytical Techniques*, S. Agrawal, Ed, Humana Press, Totowa, USA (1993); S. T. Crooke, F. Bennet, *Ann. Rev. Pharmacol. Toxicol.* 36:107–129 (1996); and J. Hunziker and C. Leuman, Mod. Synt. Methods 7:331–417 (1995).

For example, in comparison to natural DNA, a phosphodiester internucleoside bridge, a β-D-2'-deoxyribose unit, and/or a natural nucleoside base (adenine, guanine, cytosine, thymine) can be modified or replaced, respectively. An oligonucleotide according to the invention can have one or more modifications, wherein each modification is located at a particular phosphodiester internucleoside bridge, and/or at a particular β-D-2'-deoxyribose unit, and/or at a particular natural nucleoside base position in comparison to an oligonucleotide of the same sequence which is composed of natural DNA.

For example, the invention relates to an oligonucleotide, which comprises one or more modifications and wherein each modification is independently selected from:

a) the replacement of a phosphodiester internucleoside bridge located at the 3'- and/or the 5'-end of a nucleoside by a modified internucleoside bridge, b) the replacement of a phosphodiester bridge located at the 3'- and/or the 5'-end of a nucleoside by a dephospho bridge, c) the replacement of a sugar phosphate unit from the sugar phosphate backbone by another unit, d) the replacement of a β-D-2'-deoxyribose unit by a modified sugar unit, e) the replacement of a natural nucleoside base by a modified nucleoside base, f) the conjugation to a molecule which influences the properties of the oligonucleotide, g) the conjugation to a 2'5'-linked oligoadenylate or a derivative thereof, optionally via an appropriate linker, and h) the introduction of a 3'—3' and/or a 5'—5' inversion at the 3'- and/or the 5'-end of the oligonucleotide.

More detailed examples for the chemical modification of an oligonucleotide are a) the replacement of a phosphodiester internucleoside bridge located at the 3'- and/or the 5'-end of a nucleoside by a modified internucleoside bridge, wherein the modified internucleoside bridge is, for example, selected from phosphorothioate, phosphorodithioate, $NR^1R^1$-phosphoramidate, boranophosphate, phosphate-$(C_1-C_{21})$—O-alkyl ester, phosphate-[$(C_6-C_{12})$-aryl-$((C_1-C_{21})$—O-alkyl]ester, $(C_1-C_8)$-alkyl-phosphonate and/or $(C_6-C_{12})$arylphosphonate bridges and $(C_7-C_{12})$-α-hydroxymethyl-aryl (e.g., disclosed in WO 95/01363), wherein $(C_6-C_{12})$-aryl, $(C_6-C_{20})$-aryl and $(C_6-C_{14})$-aryl are optionally substituted by halogen, alkyl, alkoxy, nitro or cyano, and where $R^1$ and $R^{1'}$ are, independently of each other, hydrogen, $(C_1-C_{18})$-alkyl, $(C_6-C_{20})$-aryl, $(C_6-C_{14})$-aryl-$(C_1-C_8)$-alkyl, preferably hydrogen, $(C_1-C_8)$-alkyl, preferably $(C_1-C_4)$-alkyl and/or methoxyethyl, or $R^1$ and $R^{1'}$, together with the nitrogen atom carrying them, form a 5- to 6-membered heterocyclic ring, which can additionally contain a further heteroatom from the group O, S and N, b) the replacement of a phosphodiester bridge located at the 3'- and/or the 5'-end of a nucleoside by a dephospho bridge (dephospho bridges are described, for example, in Uhlmann, E. and Peyman, A. in *Methods in Molecular Biology*, Vol. 20, "Protocols for Oligonucleotides and Analogs", S. Agrawal, Ed., Humana Press, Totowa (1993), Chapter 16, 355ff), wherein a dephospho bridge is, for example, formacetal, 3'-thioformacetal, methylhydroxylamine, oxime, methylenedimethylhydrazo, dimethylenesulfone, and/or a silyl group;

c) the replacement of a sugar phosphate unit (β-D-2'-deoxyribose and phosphodiester internucleoside bridge together form a sugar phosphate unit) from the sugar phosphate backbone (sugar phosphate backbone is composed of sugar phosphate units) by another unit, wherein the other unit is, for example, suitable to build up a "morpholino-derivative" oligomer (as described, for example, in E. P. Stirchak et al., Nucleic Acids Res. 17 (1989) 6129), that is, e.g., the replacement by a morpholino-derivative unit;

a polyamide nucleic acid ("PNA") (as described, for example, in P. E. Nielsen et al., Bioconj. Chem. 5 (1994) 3 and in EP 0672677 A2); that is, e.g., the replacement by a PNA backbone unit, e.g., by 2-aminoethylglycine;

a phosphonic acid monoester nucleic acid ("PHONA") as described, e.g., in Peyman et al., *Angew. Chem. Int. Ed. Engl.* 35:2632–2638 (1996) and in EP 0739898 A2; that is, e.g., the replacement by a PHONA backbone unit;

d) the replacement of a βD-2'-deoxyribose unit by a modified sugar unit, wherein the modified sugar unit is, for example, selected from β-D-ribose, α-D-2'-deoxyribose, L-2'-deoxyribose, 2'-F-2'-deoxyribose, 2'-O-$(C_1-C_6)$-alkylribose, the preferred 2'-O—$(C_1-C_6)$-alkylribose being 2'-O-methylribose, 2'-O—$(C_2-C_6)$-alkenylribose, 2'-[O—$(C_1-C_6)$-alkyl-O—$(C_1-C_6)$-alkyl]ribose, 2'-NH$_2$-2'-deoxyribose, β-D-xylo-furanose, α-arabinofuranose, 2,4-dideoxy-β-D-erythro-hexo-pyranose, and carbocyclic (described, for example, in Froehler, *J. Am. Chem. Soc.* 114:8320 (1992)) and/or open-chain sugar analogs (described, for example, in Vandendriessche et al., Tetrahedron 49:7223 (1993)) and/or bicyclosugar analogs (described, for example, in M. Tarkov et al., *Helv. Chim. Acta* 76:481 (1993));

e) the replacement of a natural nucleoside base by a modified nucleoside base, wherein the modified nucleoside base is, for example, selected from uracil, hypoxanthine, 5-(hydroxymethyl)uracil, $N^2$-dimethylguanosine, pseudouracil, 5-(hydroxymethyl)uracil, 5-aminouracil, dihydrouracil, 5-fluorouracil, 5-fluorocytosine, 5-chlorouracil, 5-chlorocytosine, 5-bromouracil, 5-bromocytosine, 2,4-diaminopurine, 8-azapurine, a substituted 7-deazapurine, preferably 7-deaza-7-substituted and/or 7-deaza-8-substituted purine or other modifications of natural nucleoside bases, (modified nucleoside bases are, e.g., described in EP 0 710 667 A2 and EP 0 680 969 A2);

f) the conjugation to a molecule which influences the properties of the oligonucleotide, wherein the conjugation of the oligonucleotide to one or more molecules that favorably influence the properties of the oligonucleotide (for example, the ability of the oligonucleotide to penetrate the cell membrane or to enter a cell, the stability toward nucleases, the affinity for an eg5 encoding target sequence, the pharmacokinetics of the oligonucleotide, the ability of an antisense oligonucleotide/ribozyme or a molecule conjugated to the oligonucleotide respectively to attack the eg5 encoding target sequence, e.g., the ability to bind to and/or to crosslink, when the oligonucleotide hybridizes with the eg5 encoding target sequence). Examples of molecules that can be conjugated to an oligonucleotide are (1) polylysine, (2) intercalating agents such as pyrene, acridine, phenazine, or phenanthridine, (3) fluorescent agents such as fluorescein, (4) crosslinking agents such as psoralen or azidoproflavin, (5) lipophilic molecules such as ($C_{12}$–$C_{20}$)-alkyl, (6) lipids such as 1,2-dihexadecyl-rac-glycerol, (7) steroids such as cholesterol or testosterone, (8) vitamins such as vitamin E, (9) poly- or oligoethylene glycol, preferably linked to the oligonucleotide via a phosphate group (e.g., triethylene glycol phosphate, hexaethylene glycol phosphate), (10) ($C_{12}$–$C_{18}$)-alkyl phosphate diesters, and/or (11) O—$CH_2$—CH(OH)—O—($C_{12}$–$C_{18}$)alkyl, these molecules can be conjugated at the 5'-end and/or the 3'-end and/or within the sequence, e.g., to a nucleoside base in order to generate an oligonucleotide conjugate; processes for preparing an oligonucleotide conjugate are known to the skilled person and are described, for example, in Uhlmann, E. & Peyman, A., *Chem. Rev.* 90:543 (1990), M. Manoharan in *Antisense Research and Applications*, Crooke and Lebleu, Eds., CRC Press, Boca Raton (1993) Chapter 17, p. 303ff. and EP-A 0 552 766;

g) the conjugation to a 2'5'-linked oligoadenylate, preferably via an appropriate linker molecule, wherein the 2'5'-linked oligoadenylate is, for example, selected from 2'5'-linked triadenylate, 2'5'-linked tetraadenylate, 2'5'-linked pentaadenylate, 2'5'-linked hexaadenyltate, or 2'5'-linked heptaadenylate molecules and derivatives thereof, wherein a 2'5'-linked oligoadenylate derivative is, for example, Cordycepin (2'5'-linked 3'-deoxyadenylate) and wherein an example for an appropriate linker is triethylene glycol and wherein the 5'-end of the 2'5'-linked oligoadenylate must bear a phosphate, diphosphate, or triphosphate residue in which one or more oxygen atoms can be replaced, e.g., by sulfur atoms, wherein the substitution by a phosphate or thiophosphate residue is preferred; and h) the introduction of a 3'-3' and/or a 5'-5' inversion at the 3'- and/or the 5'-end of the oligonucleotide, wherein this type of chemical modification is known to the skilled person and is described, for example, in M. Koga et al., *J. Org. Chem.* 56:3757 (1991), EP 0 464 638, and EP 0 593 901.

The replacement of a sugar phosphate unit from the sugar phosphate backbone by another unit, which can be, e.g., a PNA backbone unit or a PHONA backbone unit, is preferably the replacement of a nucleotide by, e.g., a PNA unit or a PHONA unit, which already comprises natural nucleoside bases and/or modified nucleoside bases, e.g., one of the modified nucleoside bases from the group of uracil, hypoxanthine, 5-(hydroxy-methyl)uracil, $N^2$-dimethylguanosine, pseudouracil, 5-(hydroxymethyl)uracil, 5-aminouracil, pseudouracil, dihydrouracil, 5-fluorouracil, 5-fluorocytosine, 5-chlorouracil, 5-chlorocytosine, 5-bromouracil, 5-bromocytosine, 2,4-diamino-purine, 8-azapurine, a substituted 7-deazapurine, preferably 7-deaza-7-substituted, and/or 7-deaza-8-substituted purine or other modifications of a natural nucleoside base (modified nucleotide bases are described in, e.g., EP 0 710 667 A2 and EP 0 680 969 A2).

The oligonucleotide modifications described in EP 0 710 667 A2, EP 0 680 969 A2, EP 0 464 638, EP 0 593 901, WO 95/01363, EP 0 672 677 A2, EP 0 739 898 A2, and EP 0 552 766 are hereby incorporated by reference.

In a special embodiment of the invention, one or more phosphodiester internucleoside bridges within the oligonucleotide sequence are modified; preferably one or more phosphodiester internucleoside bridges are replaced by phosphorothioate internucleoside bridges and/or ($C_6$–$C_{12}$)-aryl phosphonate internucleoside bridges, preferably by α-hydroxybenzyl phosphonate bridges in which the benzyl group is preferably substituted, e.g., with nitro, methyl, halogen.

In an all-phosphorothioate oligonucleotide, all phosphodiester internucleoside bridges are modified by phosphorothioate. Preferably, the invention relates to an oligonucleotide in which not all phosphodiester internucleoside bridges are modified uniformly with phosphorothioate (phosphorothioate internucleoside bridges). Preferably, at least one internucleoside bridge has a different type of modification or is not modified. In particular, the invention relates to an oligonucleotide that comprises, in addition, at least one other type of modification.

In another special embodiment of the invention, one or more nucleosides (βD-2'-deoxyribose and/or nucleoside base) within the oligonucleotide sequence are modified; preferably, the βD-2'-deoxyribose is substituted by 2'-O—($C_1$–$C_6$)alkylribose, preferably by 2'-O-methylribose and/or the nucleoside base is substituted by 8-azapurine, 7-deaza-7-substituted purine, and/or 7-deaza-8-substituted purine (purine: adenine, guanine). Preferably, the invention relates to an oligonucleotide in which not all nucleosides are modified uniformly. Preferably, the invention relates to an oligonucleotide, which comprises, in addition, at least one other type of modification.

In another special embodiment of the invention, one or more sugar phosphate units from the sugar phosphate backbone are replaced by PNA backbone units, preferably by 2-aminoethylglycine units. Preferably, the sugar phosphate units that are replaced are connected together at least to a certain extent. Preferably, the invention relates to an oligonucleotide in which not all sugar phosphate units are uniformly replaced. In particular, the invention relates to chimeric oligonucleotides, e.g., composed of one or more PNA parts and one or more DNA parts. For such chimeric oligonucleotides, for example, the following non-limiting examples of modification patterns are possible: DNA-PNA, PNA-DNA, DNA-PNA-DNA, PNA-DNA-PNA, DNA-PNA-DNA-PNA, or PNA-DNA-PNA-DNA. Comparable patterns would be possible for chimeric molecules composed of DNA parts and PHONA parts, e.g., DNA-PHONA, PHONA-DNA, DNA-PHONA-DNA, PHONA-DNA-PHONA, DNA-PHONA-DNA-PHONA, PHONA-DNA-PHONA-DNA. In addition, chimeric molecules comprising three different parts like DNA part(s), PHONA part(s) and PNA part(s) are possible. Preferably, the invention relates to an oligonucleotide, which comprises, in addition, at least one other type of modification.

In another special embodiment of the invention, the oligonucleotide is connected at its 3'-end and/or at its 5'-end to a $(C_{12}-C_{18})$-alkyl residue, preferably a $C_{16}$ alkyl residue, a triethylene glycol residue, or a hexaethylene glycol residue—these residues are preferably connected to the oligonucleotide via a phosphate group. Preferably, the invention relates to an oligonucleotide in which only one end, either the 3'- or the 5'-end, is uniformly modified. Preferably, the invention relates to an oligonucleotide that comprises, in addition, at least one other type of modification.

In a preferred embodiment of the invention, only particular positions within an oligonucleotide sequence are modified (e.g., a partially modified oligonucleotide). Partially modified oligonucleotides are also named minimal modified oligonucleotides in some documents. Within the sequence, a modification can be located at particular positions: at particular nucleotides, at particular nucleosides, at particular nucleoside bases, or at particular internucleoside bridges.

In a particular embodiment of the invention, a partially modified oligonucleotide is prepared by only replacing some of the phosphodiester bridges with modified internucleoside bridges, e.g., phosphorothioate bridges and/or α-hydroxybenzyl phosphonate bridges. In particular, the invention comprises such oligonucleotides that are only modified to a certain extent.

In particular, the invention relates to an oligonucleotide wherein the 1 to 5 terminal nucleotide units at the 5'-end and/or at the 3'-end are protected by modifying internucleoside bridges located at the 5'- and/or the 3'-end of the corresponding nucleoside, preferably by replacement of the phosphodiester internucleoside bridges by phosphorothioate bridges and/or a-hydroxybenzyl phosphonate bridges. Very particularly preferably, the 1 to 5 terminal nucleotide units at the 3'-end of the oligonucleotide are protected by modified internucleoside bridges located at the 5'- and/or the 3'-end of the corresponding nucleosides. Optionally, the 1 to 5 terminal nucleotide units at the 5'-end of the oligonucleotide are in addition protected by modified internucleoside bridges located at the 5'- and/or the 3'-end of the corresponding nucleoside. Optionally, the oligonucleotide may comprise additional modifications at other positions.

Furthermore, the invention relates to an oligonucleotide wherein at least one internal pyrimidine nucleoside and/or an internucleoside bridge located at the 5'-end and/or the 3'-end of this pyrimidine nucleoside (a nucleoside with a pyrimidine base like cytosine, uracil, thymine) is modified, preferably by replacement of the phosphodiester internucleoside bridge(s) by (a) phosphorothioate bridge(s) and/or (an) α-hydroxybenzyl phosphonate bridge(s).

In a preferred embodiment of the invention, the 1 to 5 terminal nucleotide units at the 5'-end and/or at the 3'-end of the oligonucleotide are protected by modifying internucleoside bridges located at the 5'- and/or the 3'-end of the corresponding nucleoside, and wherein, in addition, at least one internal pyrimidine nucleoside and/or an internucleoside bridge located at the 5'-end of this pyrimidine nucleoside and/or located at the 3'-end of this pyrimidine nucleoside is modified.

The principle of partially modified oligonucleotides is described, e.g., in A. Peyman, E. Uhlmann, *Biol. Chem. Hoppe-Seyler*, 377:67–70 (1996) and in EP 0 653 439. These documents are hereby incorporated by reference. In this case, the 1–5 terminal nucleotide units at the 5'-end/or at the 3'-end are protected, e.g., the phosphodiester internucleoside bridges located at the 3'- and/or the 5'-end of the corresponding nucleosides are, for example, replaced by phosphorothioate internucleoside bridges. In addition, preferably at least one internal pyrimidine nucleoside (or nucleotide respectively) position is modified; preferably the 3'- and/or the 5'-internucleoside bridge(s) of a pyrimidine nucleoside is/are modified/replaced, for example, by (a) phosphorothioate internucleoside bridge(s). Partially modified oligonucleotides exhibit particularly advantageous properties; for example, they exhibit a particularly high degree of nuclease stability in association with minimal modification. They also have a significantly reduced propensity for non-antisense effects, which are often associated with the use of all-phosphorothioate oligonucleotides (Stein and Krieg, *Antisense Res. Dev.* 4:67(1994)). Partially modified oligonucleotides also show a higher binding affinity than all-phosphorothioates.

The invention relates in particular to partially/minimally modified oligonucleotides.

SEQ ID NO. 10: 3-'C*T*T*A A G G C*A G T*A C*C G*C A G*C-5', (K3)
5'-C G A C*G*C*C*A*T G A*C G G AA*T*T*C-3';

SEQ ID NO. 11: 3'-A*C*C*A C*T C*T A C*G T*C*T G G*T A*A-5', (K4)
5'-A*AT*GGT*C*TG*CAT*CT*CA*C*C*A-3';

SEQ ID NO. 12: 3'-G*G*C*A G*T A C*C G C*A G*C G T*C G*G-5', (K6)
5'-G*G C*T G C*G A*C G C*C A T*G A*C*G*G-3';

SEQ ID NO. 13: 3'-C*T*T*A A G G*C A G*T*A-5',
5'-A*T*G A C*G G A A*T*T*C-3';

SEQ ID NO. 14: 3'-T*A*A G G C*A G*T A*C*C-5',
5'-C*C*A T*G A*C G G A*A*T-3';

SEQ ID NO. 15: 3'-G*G*C A G*T A C*C*G C*A-5',
5'-A*C G*C*C A T*G A C*G*G-3';

SEQ ID NO. 16: 3'-A*G*T A C*C G*C A G*C*G-5',
5'-G*C*G A C*G C*C A T*G*A-3';

SEQ ID NO. 17: 3'-C*C*G*C A G*C G T*C G*G-5',
5'-G*G C*T G C*G A C*G*C*C-3';

SEQ ID NO. 18 3'-G*C*A G C*G T*C G G*T*T-5',
5'-T*T*G G C*T G C*G A*C*G-3'.

wherein "*" denotes the position of an internucleoside bridge modification;

preferably "*" is a phosphorothioate internucleoside bridge.

Another example for a special embodiment of the invention relates to a partially modified oligonucleotide wherein a nucleoside is modified, e.g., a modification of a nucleotide base and/or a modification of a βD-2'-deoxyribose unit. Preferably, a βD-2'-deoxyribose is replaced by 2'-O—$(C_1-C_6)$-alkylribose; very particularly preferred is the replacement by 2'-O-methylribose (replacement of a βD-2'-deoxyribonucleoside by a 2'-O-methylribonucleoside).

According to the invention, the oligonucleotide can have, in addition to one type of modification, also other types of modification.

Therefore, in another embodiment of the invention, the oligonucleotide comprises modified internucleoside bridges at particular positions and in addition modifications of a nucleoside at particular positions, preferably the replacement of βD-2'-deoxyribose. In a preferred embodiment of the invention, the internucleoside modification is the replacement of a phosphodiester bridge by a phosphorothioate bridge and the modification of the βD-2'-deoxyribose is the replacement by 2'-O-methylribose; in this case, the oligonucleotide is a chimeric oligonucleotide, which is composed of modified and unmodified DNA and RNA parts - which comprise the 2'-O-methylribonucleosides and β-D-2'-deoxyribonucleosides and phosphoro-diester and phosphorothioate internucleoside bridges.

A further preferred embodiment of the invention provides an oligonucleotide, which has one or more $(C_{12}-C_{18})$-alkyl residues, preferably a $C_{16}$-alkyl residue at its 3'- and/or its 5'-end. A $(C_{12}-C_{18})$-alkyl residue can, e.g., be bound as a phosphodiester as described in EP 0 552 766 A2, which is hereby incorporated by reference or as a 3'- phosphodiester of O—$CH_2$—CH(OH)—O—$(C_{12}-C_{18})$-alkyl. Preferred is an oligonucleotide that has a $C_{16}$-alkyl residue bound to its 3'- and/or 5'-end.

The invention also relates to an oligonucleotide in which the 3'- and/or the 5'-end is connected to an oligoethylene glycol residue, preferably a triethylene glycol or a hexaethylene glycol, very particularly preferably via a phosphodiester (tri- or hexaethylene glycol phosphate ester). Of course, such an oligonucleotide may also comprise additional modifications.

In another specific embodiment of the invention, the oligonucleotide is connected via a linker to a 2'5'-linked oligoadenylate-5'-(thio)phosphate. The linker can, e.g., be an oligo-ethylene glycol phosphate, preferably triethylene glycol phosphate, tetra-ethylene glycol phosphate or hexa-ethylene glycol phosphate residue. The 2'5'-linked oligoadenylate is preferably attached via its 2'-end as a tetra- or as a penta-adenylate whose 5'-hydroxy function is substituted by a phosphate or thiophosphate residue. The 2'5'-oligoadenylate is known to induce RNase L to cleave the target mRNA (Torrence et al., *Proc. Natl. Acad. Sci. U.S.A.* 90:1300 (1993)). The 2'5'-oligoadenylate serves to activate ribonuclease L (RNase L) which then degrades the eg5 mRNA. Instead of a 2'5'-linked adenylate, e.g., a 2'5'-linked 3'-deoxy adenylate, derived from the nucleoside analog cordycepin, can be introduced. In this case, the oligonucleotide part, which is complementary to the target nucleic acid, is preferably modified at particular positions by 2'-O—$(C_1-C_6)$-alkylribonucleoside (preferably 2'-O-methylribonucleoside) or by PNA.

Another preferred embodiment of the invention involves the replacement of one or more natural nucleoside base(s) by non-natural or modified nucleoside bases respectively, preferably by 8-azapurines and/or 7-deaza-7-substituted purines and/or 7-deaza-8-substituted purine, e.g., as described in EP 0 171 066 and EP 0 680 969.

In another preferred embodiment of the invention, the oligonucleotide can exhibit 3'3' and/or 5'5'-inversions at the 3'- and/or 5'-end, e.g., as described in EP 0 464 638 and EP 0 593 901.

Another preferred embodiment of the invention relates to the replacement of one or more phosphodiester bridges by a-hydroxybenzyl phosphonate bridges as described in WO 95/01363.

In another preferred embodiment of the invention the oligonucleotide comprises a modification of the sugar phosphate backbone, preferably by PNA units.

Also other patterns of modification are possible, e.g., DNA-PNA-DNA, PNA-DNA. Comparable patterns of modification are also possible for PHONA/DNA chimeras. These modification patterns can be combined with any other type of modification and, of course, similar patterns of modification are also possible for other oligonucleotides according to the invention.

The above concrete oligonucleotides—particular sequence, particular type(s) of modification(s) at particular positions (specific "pattern of modification") are only examples for different embodiments of the invention. The invention is not limited to these concrete oligonucleotides. Also other combinations of sequence and pattern of modification are possible.

An oligonucleotide according to the invention specifically inhibits the expression of the target protein (which is eg5) or the target sequence (a nucleic acid which encodes eg5, preferably eg5 mRNA) respectively. Preferably, an oligonucleotide according to the invention specifically inhibits the expression of eg5. This results in a reduction in the eg5 protein level in comparison to untreated expression. The specificity can, for example, be demonstrated by determining the effect of an oligonucleotide according to the invention upon eg5 expression in comparison to the effect of the same oligonucleotide upon beta actin expression, on the mRNA and/or the protein level. Upon treatment with an oligonucleotide according to the invention only the eg5 mRNA and/or eg5 protein level is reduced, while, e.g., beta actin (a house-keeping protein) mRNA and/or beta-actin protein level remains unchanged.

Preferably, an oligonucleotide according to the invention can efficiently inhibit the expression of eg5 in human cells and/or has the ability to inhibit tumor growth in vertebrates. Preferably, an oligonucleotide according to the invention reduces the eg5 mRNA and/or protein level in tumors of treated individuals relative to untreated individuals. Preferably, an oligonucleotide according to the invention reduces tumor volume in a vertebrate, e.g., in mice compared to untreated mice or relative to the tumor volume of the same animal determined before treatment.

The invention also relates to a method for the preparation of an oligonucleotide according to the invention. A method for preparation comprises the chemical synthesis of the oligonucleotide. Preferably, the chemical synthesis is performed by a standard method known to be used for the synthesis of oligonucleotides, e.g., the phoshoramidite method according to Caruthers (1983) Tetrahedron Letters 24, 245, the H-phosphonate method (Todd et al., *J. Chem. Soc.* 3291(1957)) or the phosphotriester method (Sonveaux, Bioorg. Chem. 14:274 (1986); Gait, M.J. "*Oligonucleotide Synthesis, A Practical Approach*", IRL Press, Oxford, 1984) or improved or varied methods derived from these standard methods. An oligonucleotide according to the invention can, for example, be prepared as described in Example 1. Preferably, an oligonucleotide according to the invention is synthesized on a solid phase by condensing suitably protected monomers (e.g., nucleosides) in order to form internucleoside bridges between these monomers.

The invention relates, e.g., to a method for preparing an oligonucleotide or a derivative thereof, where a nucleotide unit with a 3'- or a 2'-terminal phosphorus (V) group and a free 5'-hydroxyl or mercapto grouping is reacted with a further nucleotide unit with a phosphorus (III) or a phosphorus (V) grouping in the 3'-position, or its activated derivatives, and wherein optionally protective groups are used, which can be temporarily introduced in the oligonucleotide in order to protect other functions and which are removed after synthesis, and the oligonucleotide which has been cleaved from the solid phase can optionally be converted into a physiologically tolerated salt. In order to synthesize a modified oligonucleotide, standard methods are varied to a certain extent. Those variations are known to a person of skill in the art and are described, e.g., in Agrawal S., Protocols for oligonucleotides and analogs (1993), Human Press Inc., Totowa, New Jersey). The preparation of modified oligonucleotides is also described in EP 0 710 667, EP 0 680 969, EP 0 464 638, EP 0 593 901, WO 95/01363, EP 0 672 677, EP 0 739 898 and EP 0 552 766. The methods of preparing modified oligonucleotides described in the above documents are hereby incorporated by reference.

The invention further relates to a method of inhibiting the expression of eg5 and/or modulating the expression of an eg5 encoding nucleic acid, wherein an oligonucleotide according to the invention is brought into contact with an eg5 encoding nucleic acid (e.g., mRNA, cDNA) and the oligonucleotide is hybridized with this eg5 encoding nucleic acid.

Therefore, the invention also relates to a method wherein the oligonucleotide is brought into contact with an eg5 encoding nucleic acid (e.g., mRNA; cDNA), for example, by introducing the oligonucleotide into a cell by known methods, for example, by incubation of cells with said oligonucleotide or a formulation thereof—such a formulation may comprise uptake enhancers, such as lipofectin, lipofectamine, cellfectin or polycations (e.g., polylysine).

For example, an oligonucleotide which was incubated previously with cellfectin for, e.g., 30 minutes at room temperature is then incubated about 5 hours or less with a cell in order to introduce the oligonucleotide into the cell.

The invention further relates to the use of the oligonucleotide, preferably as antisense oligonucleotide (binding of the oligonucleotide to an eg5 encoding mRNA) or as ribozyme (binding to an eg5 encoding mRNA and cleavage of this mRNA). In another special embodiment of the invention, the oligonucleotide can be used to induce RNAse H cleavage of the eg5 encoding mRNA, thus resulting in a reduction in eg5 expression.

The invention relates to the use of an oligonucleotide for inhibiting formation of a bipolar mitotic spindle and therefore for inhibiting cell proliferation, especially tumor growth.

The invention furthermore relates to the use of the oligonucleotide as pharmaceutical and to the use of the oligonucleotide for preparing a pharmaceutical composition. In particular, the oligonucleotide can be used in a pharmaceutical composition that is employed for preventing and/or treating diseases which are associated with the expression of eg5, or which can be cured by the inhibition of eg5 expression.

The invention furthermore relates to a pharmaceutical composition that comprises an oligonucleotide and/or its physiologically tolerated salts in addition to pharmaceutically unobjectable excipients or auxiliary substances.

The invention relates to a pharmaceutical composition that comprises at least one oligonucleotide according to the invention that can be used for the treatment of diseases which can be cured by inhibition of eg5 expression, such as restenosis and cancer.

The invention further relates to a method for preparing a pharmaceutical composition, which comprises mixing of one or more oligonucleotides according to the invention with physiologically acceptable excipients and optionally additional substances, e.g., if appropriate with suitable additives and/or auxiliaries.

The invention relates in particular to the use of an oligonucleotide or a pharmaceutical composition prepared therefrom for the treatment of cancer, e.g., for inhibiting tumor growth and tumor metastasis. For example, the oligonucleotide or a pharmaceutical composition prepared therefrom may be used for the treatment of solid tumors, like breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma and for the treatment of skin cancer, like melanoma, for the treatment of lymphomas and blood cancer. The invention further relates to the use of an oligonucleotide according to the invention or a pharmaceutical composition prepared therefrom for inhibiting eg5 expression and/or for inhibiting accumulation of ascites fluid and pleural effusion in different types of cancer, e.g., breast cancer, lung cancer, head cancer, neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma, skin cancer, melanoma, lymphomas and blood cancer. Owing to the inhibitory effect on eg5 expression, an oligonucleotide according to the invention or a pharmaceutical composition prepared therefrom can enhance the quality of life.

The invention furthermore relates to the use of an oligonucleotide or a pharmaceutical composition thereof, e.g., for treating cancer or for preventing tumor metastasis, in combination with other pharmaceuticals and/or other therapeutic methods, e.g., with known pharmaceuticals and/or known therapeutic methods, such as, for example, those which are currently employed for treating cancer and/or for preventing tumor metastasis. Preference is given to a combination with radiation therapy and chemotherapeutic agents, such as cisplatin, cyclophosphamide, 5-fluorouracil, adriamycin, daunorubicin or tamoxifen.

The oligonucleotide and/or its physiologically tolerated salt can be administered to an animal, preferably a mammal, and in particular a human, on its own, in a mixture with another oligonucleotide (or its physiologically tolerated salt), or in the form of a pharmaceutical composition which permits topical, percutaneous, parenteral or enteral use and which comprises, as the active constituent, an effective dose of at least one oligonucleotide, in addition to customary pharmaceutically unobjectionable excipients and auxiliary substances. Such a pharmaceutical composition normally comprises from about 0.1 to 90% by weight of the therapeutically active oligonucleotide(s). The dose can vary within wide limits and is to be adjusted to the individual circumstances in each individual case. In order to treat psoriasis, preference is given to a topical use. In the case of cancer, preference is given to infusions, oral and rectal administration, or nasal application in an aerosol, preferable in the case of lung cancer, while in the case of diabetic retinopathy, preference is given to a topical, intravitreal and oral administration.

A pharmaceutical composition can be prepared in a manner known per se (e.g., Remingtons Pharmaceutical Sciences, Mack Publ. Co., Easton, Pa. (1985)), with pharmaceutically inert inorganic and/or organic excipients being used. Lactose, cornstarch and/or derivatives thereof, talc, stearic acid and/or its salts, etc. can, for example, be used for preparing pills, tablets, film-coated tablets and hard gelatin capsules. Examples of excipients for soft gelatin capsules and/or suppositories are fats, waxes, semisolid and liquid polyols, natural and/or hardened oils, etc. Examples of suitable excipients for preparing solutions and/or syrups are water, sucrose, invert sugar, glucose, polyols, etc. Suitable excipients for preparing injection solutions are water, alcohols, glycerol, polyols, vegetable oils, etc. Suitable excipients for microcapsules, implants and/or rods are mixed polymers of glycolic acid and lactic acid. In addition, there are liposome formulations which are, e.g., described in N. Weiner (Drug Develop Ind Pharm 15 (1989)1523), "Liposome Dermatics" (Springer Verlag 1992) and Hayashi (Gene Therapy 3 (1996) 878). The pharmaceutical composition may also comprise a formulation, which enhances the oral availability of the oligonucleotide, such as enhancers of intestinal absorption, e.g., mannitol, urea, bile salts, such as CDCA (chenodeoxycholate) (2%).

Dermal administration can also be effected, for example, using ionophoretic methods and/or by means of electroporation. Furthermore, use can be made of lipofectins and other carrier systems, for example, those used in gene therapy. Systems, which can be used to introduce oligonucleotides in a highly efficient manner into eukaryotic cells or into the nuclei of eukaryotic cells, are particularly suitable. A pharmaceutical composition may also comprise two or more different oligonucleotides and/or their physiologically tolerated salts and, furthermore, in addition to at least one oligonucleotide, one or more different therapeutic active ingredients.

In addition to the active ingredients and excipients, a pharmaceutical composition can also comprise additives, such as fillers, extenders, disintegrants, binders, lubricants, wetting agents, stabilizing agents, emulsifiers, preservatives, sweeteners, dyes, flavorings or aromatizing agents, thickeners, diluents or buffering substances, and, in addition, solvents and/or solubilizing agents and/or agents for achieving a slow release effect, and also salts for altering the osmotic pressure, coating agents and/or antioxidants.

EXAMPLES

Example 1

Oligonucleotide Synthesis

Oligonucleotides ("ON s") were synthesized using an Applied Biosystems 394 DNA synthesizer (Perkin Elmer Applied Biosystems, Inc., Foster City, USA) and standard phosphoramidite chemistry. After coupling, phosphorothioate linkages were introduced by sulfurization using the Beaucage reagent followed by capping with acetic anhydride and N-methylimidazole. After cleavage from the solid support and final deprotection by treatment with concentrated ammonia, ON s were purified by polyacrylamide gel electrophoresis. The 2'-O-methyl modified ON s were prepared by replacing the standard phosphoramidites in the corresponding cycle with 2'-O-methyl ribonucleoside phophoramidites. All ON s were analyzed by negative ion electrospray mass spectroscopy (Fisons Bio-Q) which in all cases confirmed the calculated mass. The C16-modified oligonucleotides were synthesized using hexadecyloxy (cyanoethoxy)-N,N-diisopropyl-aminophosphane as phosphitylating reagent in the last step of oligonucleotide synthesis in place of a standard amidite, or by starting from a correspondingly derivatized solid support. The triethylene glycol linker is commercially available from Glen Research Corporation. The 2'-phosphoramidites of adenosine or cordycepin were obtained from Chem. Genes Corporation and Chemogen Corporation, respectively. The introduction of 5'-phosphates or thiophosphate residues was carried out as described previously (Uhlmann and Engels (1986) Tetrahedron Lett. 27, 1023). The PNA-DNA chimeras are prepared as described in EP 0 672 677.

Analysis of the oligonucleotides was done by
a) analytical gel electrophoresis in 20% acrylamide, 8M urea, 45 µM tris-borate buffer, pH 7.0 and/or
b) HPLC analysis: Waters GenPak FAX column, gradient $CH_3CN$ (400 mM), $H_2O$ (1.6l), $NaH_2PO_4$ (3.1 g), NaCl (11.7 g), pH6.8 (0.1 M NaCl) after $CH_3CN$ (400ml), $H_2O$ (1.6l), $NaH_2PO4$ (3.1 g), NaCl (17.53 g), pH6.8 (1.5M NaCl) and/or
c) capillary electrophoresis using a Beckmann eCAP™, U100P gel capillary column, 65 cm length, 100 mm Internal Diameter, window 15 cm from one end, buffer 140 µM Tris, 360 mM borate, 7M urea and/or
d) negative ion electrospray mass spectrometry which in all cases confirmed the expected mass values.

The methods for analyzing oligonucleotides according to a), b), c) and d) are known to a person of skill in the art. These methods are, for example, described in Schweitzer and Engels "Analysis of oligonucleotides" (in "Antisense - from technology to therapy", a laboratory manual and textbook, Schlingensiepen et al. eds., Biol. Science, 6:78–103 (1997)).

The following oligonucleotides were prepared (see description) and tested:

ON1: 3-'C*T*T*A AG G C*A G T*A C*C G*C A G*C (K3) Seq. ID NO.10

ON2: 3'-A*C*C*A C*T C*T A C*G T*C*T G G*T A*A (K4) Seq. ID NO.11

ON3: 3'-A*A*G*A G*T C*A C*T C*T C*C*T A G G*C (K5) Seq. ID NO.19

ON4: 3-'C*T*T*A A G G C*A G T*A C*C G*C A G*C-FITC-5' Seq. ID NO.10

ON5: 3'-G*G*C A G*T A C*C G*C A G C*G Seq. ID NO. 22

ON6: 3'-C*T*T*A A G G*C A G*T*A Seq. ID NO.13

ON7: 3'-T*A*A G G C*A G*T A*C*C Seq. ID NO.14

ON8: 3'-G*G*C A G*T A C*C*G C*A Seq. ID NO. 15

ON9: 3'-C*A*G*T A C*C G*C A G*C Seq. ID NO. 23

ON10: 3'-A*G*T A C*C G*C A G*C*G Seq. ID NO. 16

ON11: 3'-C*C*G*C A G*C G T*C G*G Seq. ID NO. 17

ON12: 3'-G*C*A G C*G T*C G G*T*T Seq. ID NO. 18

ON13: 3'-A*A*G*A G*T C*A C*T C*T C*C*T A G G*C-FITC-5' (comparison 1) Seq. ID NO. 19

ON14: 3'-G*G*C*A G*T A C*C G C*A G*C G T*C G*G Seq. ID NO. 12

ON15: 3'-C*T*T*A A G G*C A G*T*A-FITC Seq. ID NO. 13 wherein

"*" is a phosphorothioate internucleoside bridge, and FITC is a fluorescence label.

ON1 to ON 12 were tested in a cell-based assay for their effectiveness in inhibiting the proliferation of REH leukemia cells. ON1, ON2, ON4–ON12, ON 14, ON15 are antisense oligonucleotides directed against the translational start region of eg5 mRNA. ON4 is the 5'-fluoresceine labeled analog of ON1. ON3 is a comparison oligonucleotide.

The results of the proliferation inhibition experiment are shown in FIG. 1.

Example 2

Determination of the antiproliferative activity of the eg5 antisense oligonucleotides The REH cells (human pre-B leukemia cells, DSM ACC 22) or the A549 tumor cells were cultivated inOptiMEM (Gibco BRL) with 10% fetal calf serum (FCS, GIBCO-BRL) at 37° C. under 5% $CO_2$. The cell density for the assay was about 1×106/ml. The oligonucleotides (0.17 mM ) were mixed with cellfectin (0.83 mg/ml; Gibco-BRL) for complex formation to improve cellular uptake. The oligonucleotide/cellfectin complex was incubated with the cells in 24-well plates for 4 hours in the absence of serum. The oligonucleotide/cellfectin complex was then removed and serum was added to a final concentration of 10%. After 96 hours' incubation at 37° C. under 5% $CO_2$ the cell density was measured with Casy 1 (from Scharfe). For this, the cells in each well were mixed thoroughly and immediately diluted 1:100 with Casyton. Mean values of cell density were determined in each case from 3 individual wells of the same oligonucleotide concentration. The results of the antiproliferative activity are depicted in FIG. 1.

TABLE 1

Nucleotide sequence of human eg5 (SEQ ID NO.20)

```
   1 GAATTCCGTC ATGGCGTCGC AGCCAAATTC GTCTGCGAAG AAGAAAGAGG
  51 AGAAGGGGAA GAACATCCAG GTGGTGGTGA GATGCAGACC ATTTAATTTG
 101 GCAGAGCGGA AAGCTAGCGC CCATTCAATA GTAGAATGTG ATCCTGTACG
 151 AAAAGAAGTT AGTGTACGAA CTGGAGGATT GGCTGACAAG AGCTCAAGGA
 201 AAACATACAC TTTTGATATG GTGTTTGGAG CATCTACTAA ACAGATTGAT
 251 GTTTACCGAA GTGTTGTTTG TCCAATTCTG GATGAAGTTA TTATGGGCTA
 301 TAATTGCACT ATCTTTGCGT ATGGCCAAAC TGGCACTGGA AAAACTTTTA
 351 CAATGGAAGG TGAAAGGTCA CCTAATGAAG AGTATACCTG GGAAGAGGAT
 401 CCCTTGGCTG GTATAATTCC ACGTACCCTT CATCAAATTT TTGAGAAACT
 451 TACTGATAAT GGTACTGAAT TTTCAGTCAA AGTGTCTCTG TTGGAGATCT
 501 ATAATGAAGA GCTTTTTGAT CTTCTTAATC CATCATCTGA TGTTTCTGAG
 551 AGACTACAGA TGTTTGATGA TCCCCGTAAC AAGAGAGGAG TGATAATTAA
 601 AGGTTTAGAA GAAATTACAG TACACAACAA GGATGAAGTC TATCAAATTT
 651 TAGAAAAGGG GGCAGCAAAA AGGACAACTG CAGCTACTCT GATGAATGCA
 701 TACTCTAGTC GTTCCCACTC AGTTTTCTCT GTTACAATAC ATATGAAAGA
 751 AACTACGATT GATGGAGAAG AGCTTGTTAA AATCGGAAAG TTGAACTTGG
 801 TTGATCTTGC AGGAAGTGAA AACATTGGCC GTTCTGGAGC TGTTGATAAG
 851 AGAGCTCGGG AAGCTGGAAA TATAAATCAA TCCCTGTTGA CTTTGGGAAG
 901 GGTCATTACT GCCCTTGTAG AAAGAACACC TCATGTTCCT TATCGAGAAT
 951 CTAAACTAAC TAGAATCCTC CAGGATTCTC TTGGAGGGCG TACAAGAACA
1001 TCTATAATTG CAACAATTTC TCCTGCATCT CTCAATCTTG AGGAAACTCT
1051 GAGTACATTG GAATATGCTC ATAGAGCAAA GAACATATTG AATAAGCCTG
1101 AAGTGAATCA GAAACTCACC AAAA AGCTC TTATTAAGGA GTATACGGAG
1151 GAGATAGAAC GTTTAAAACG AGATCTTGCT GCAGCCCGTG AGAAAAATGG
1201 AGTGTATATT TCTGAAGAAA ATTTTAGAGT CATGAGTGGA AAATTAACTG
1251 TTCAAGAAGA GCAGATTGTA GAATTGATTG AAAAAATTGG TGCTGTTGAG
1301 GAGGAGCTGA ATAGGGTTAC AGAGTTGTTT ATGGATAATA AAAATGAACT
1351 TGACCAGTGT AAATCTGACC TGCAAAATAA AACACAAGAA CTTGAAACCA
1401 CTCAAAAACA TTTGCAAGAA ACTAAATTAC AACTTGTTAA AGAAGAATAT
1451 ATCACATCAG CTTTGGAAAG TACTGAGGAG AAACTTCATG ATGCTGCCAG
1501 CAAGCTGCTT AACACAGTTG AAGAAACTAC AAAAGATGTA TCTGGTCTCC
1551 ATTCCAAACT GGATCGTAAG AAGGCAGTTG ACCAACACAA TGCAGAAGCT
1601 CAGGATATTT TTGGCAAAAA CCTCAATAGT CTGTTTAATA ATATGGAAGA
```

TABLE 1-continued

Nucleotide sequence of human eg5 (SEQ ID NO.20)

1651 ATTAATTAAG GATGGCAGCT CAAAGCAAAA GGCCATGCTA GAAGTACATA
1701 AGACCTTATT TGGTAATCTG CTGTCTTCGA GTGTCTCTGC ATTAGATACC
1751 ATTACTACAG TAGCACTTGG ATCTCTCACA TCTATTCCAG AAAATGTGTC
1801 TACTCATGTT TCTCAGATTT TTAATATGAT ACTAAAAGAA CAATCATTAG
1851 CAGCAGAAAG TAAAACTGTA CTACAGGAAT TGATTAATGT ACTCAAGACT
1901 GATCTTCTAA GTTCACTGGA AATGATTTTA TCCCCAACTG TGGTGTCTAT
1951 ACTGAAAATC AATAGTCAAC TAAAGCATAT TTTCAAGACT TCATTGACAG
2001 TGGCCGATAA GATAGAAGAT CAAAAAAAAA GGAACTCAGA TGGCTTTCTC
2051 AGTATACTGT GTAACAATCT ACATGAACTA CAAGAAAATA CCATTTGTTC
2101 CTTGGTTGAG TCACAAAAGC AATGTGGAAA CCTAACTGAA GACCTGAAGA
2151 CAATAAAGCA GACCCATTCC CAGGAACTTT GCAAGTTAAT GAATCTTTGG
2201 ACAGAGAGAT TCTGTGCTTT GGAGGAAAAG TGTGAAAATA TACAGAAACC
2251 ACTTAGTAGT GTCCAGGAAA ATATACAGCA GAAATCTAAG GATATAGTCA
2301 ACAAAATGAC TTTTCACAGT CAAAAATTTT GTGCTGATTC TGATGGCTTC
2351 TCACAGGAAC TCAGAAATTT TAACCAAGAA GGTACAAAAT TGGTTGAAGA
2401 ATCTGTGAAA CACTCTGATA AACTCAATGG CAACCTGGAA AAAATATCTC
2451 AAGAGACTGA ACAGAGATGT GAATCTCTGA ACACAAGAAC AGTTTATTTT
2501 TCTGAACAGT GGGTATCTTC CTTAAATGAA AGGGAACAGG AACTTCACAA
2551 CTTATTGGAG GTTGTAAGCC AATGTTGTGA GGCTTCAAGT TCAGACATCA
2601 CTGAGAAATC AGATGGACGT AAGGCAGCTC ATGAGAAACA GCATAACATT
2651 TTTCTTGATC AGATGACTAT TGATCAAGAT AAATTGATAG CACAAAATCT
2701 AGAACTTAAT GAAACCATAA AAATTGGTTT GACTAAGCTT AATTGCTTTC
2751 TGGAACAGGA TCTGAAACTG GATATCCCAA CAGGTACGAC ACCACAGAGG
2801 AAAAGTTATT TATACCCATC AACACTGGTA AGAACTGAAC CACGTGAACA
2851 TCTCCTTGAT CAGCTGAAAA GGAAACAGCC TGAGCTGTTA ATGATGCTAA
2901 ACTGTTCAGA AAACAACAAA GAAGAGACAA TTCCGGATGT GGATGTAGAA
2951 GAGGCAGTTC TGGGGCAGTA TACTGAAGAA CCTCTAAGTC AAGAGCCATC
3001 TGTAGATGCT GGTGTGGATT GTTCATCAAT TGGCGGGGTT CCATTTTTCC
3051 AGCATAAAAA ATCACATGGA AAAGACAAAG AAAACAGAGG CATTAACACA
3101 CTGGAGAGGT CTAAAGTGGA AGAAACTACA GAGCACTTGG TTACAAAGAG
3151 CAGATTACCT CTGCGAGCCC AGATCAACCT TTAATTCACT TGGGGGTTGG
3251 CAATTTTATT TTTAAAGAAA AACTTAAAAA TAAAACCTGA AACCCCAGAA
3251 CTTGAGCCTT GTGTATAGAT TTTAAAAGAA TATATATATC AGCCGGGCGC
3301 GTGGCTCTAG CTGTAATCCC AGCTAACTTT GGAGGCTGAG GCGGGTGGAT
3351 TGCTTGAGCC CAGGAGTTTG AGACCAGCCT GGCCAACGTG CGCTAAAACC
3401 TTCGTCTCTG TTAAAAATTA GCCGGGCGTG GTGGGCACAC TCCTGTAATC
3451 CCAGCTACTG GGGAGGCTGA GGCACAGAGA TCACTTGAAC CCAGAAGCGG
3501 GGTTGCAGTG AGCCAAAGGT ACACCACTAC ACTCCAGCCT GGGCAACAGA

TABLE 1-continued

Nucleotide sequence of human eg5 (SEQ ID NO.20)

3551 GCAAGACTCG GTCTCAAAAA TAAAATTTAA AAAAGATATA AGGCAGTACT

3601 GTAAATTCAG TTGAATTTTG ATATCTACCC ATTTTTCTGT CATCCCTATA

3651 GTTCACTTTG TATTAAATTG GGTTTCATTT GGGATTTGCA ATGTAAATAC

3701 GTATTTCTAG TTTTCATATA AAGTAGTTCT TTTAGGAATT C

TABLE 2

SEQ ID NO. 21: Sequence of P. falciparum (partial sequence; Genbank, ID Z98551).

TTTTTTTTTTTTTATTCCTTGGATGTTCTTGGTAGTTTAAATTTTTTATTTTTGTAGTTTTCTTC

TTTTATACGTTTTAAAGCAGGGGATGCCTTTTTAGGAAATGCCCTATTTTCAATAGCTTTAATTT

TTGTAGATTGAAATTTATTATTATTATTATTATTATTGTTGTTGTTGTTGTTGTTGTTGTTGTTG

TTATTATTTGAATAATTATTTGTTATATGAACATTTTGAACATTTATATTTCTCTTTCTTTCATA

TTCTTTTAAACTTGTTACACTCATATTTTCTGTATTTACATCAAATCTTTTATTATGTTGATTGT

TATTTAAATAATTTAATTCTTGATATGTTTCATCTATTGGTTGTATAGGATTATCCGTTGTATTC

TTATTATATAGCATATATTCATTTAAGGGTAGATTATTGTGATTAGTTTTTACATTTAATTTATT

TTTATCACCTTTATTATTTATATTATGAGGTATACTACTATTCGTTGTATGATCATTTAAACTAT

TGTAACGAGAGTAATTATTTTCATGCGCTACAATTTTATCATCTTGAATAAGAAATTGGAAGTTT

TCATCGATTTGTTCAAATACTTTACTTAAATCTATATCATGTGTTGTTGTAATTTGTTCTATCTC

TTTCATCAAGGTATTTTTAACTTCCAAGTATAAATTTTGTCTTATGATATCATCATTATAAAGAT

AATAATTATGATGATCACCTTGATCTATTTTATTATCATCATTATAAAGATAATAATTATGATGA

TCACCTTGATCCATTTTATTATCATCATTATAAAGATAATTATTATGATCATGACCTTGATCCAT

TTTATTATCATCATTATAAAGATAATTATTATGATCATGACCTTGATCCATTTTATTATCATCAT

TATAAAGATAATTATTATGATCATGACCTTGATCCATTTTATTATCATCATAATTATTATTGTCA

CCATTTTTATTATTGTCATGATCATTTTTATTATTGTCACCATTTTTATTATTATCATGATTATT

TTTATTATTATCATGATTATTTTTATTATTATCATGATTATTTTTATTATTATCATCATTTTTAT

TATTATCATAATTCGTGTCGTAAGTCGAATCCCTATTTAGTGATGTGATTTTCATCGGAGTAAAC

ATATCTATGACATTCACAAACGTTTCCCTTATCCTTTGTACATCATCCTTTATATTTAGATAAAA

TTCATCATCCATATTTTCCATGAGATCATAACTTGATGTACTTGGAATGTCTTGTAAGTAATCTT

TTTTTTTTAATATATCTATTAATTCTGCTATATACATATTACATTTGTTTAAATTTTGTTCAAAT

ATATTATTAAAAAGTTTTATATTTTCATTAGACTTTAACATATGTATACGACGTCCCCCTTTTG

TTCTTGTGATTCTTTATTTTTATTTTGTAAAATCTTTTCAGATATAACGTTATATAACTTTCGTT

TCTCTATTTTGTTTATATTAGTTTGACTTGTAAAGTTATTTATGATTTTATCAATATTTAGATTA

TTTGTATATAATAAATTATTATAAATATTTAAAGTATCATTTAAACATTTGCTGTGTTCCTTTTC

TTCAATATAACTTTTTCTTTTTAAATAAGATAATATGTTATATAAAACAGTATGATAATTTGTTA

TCTTCCTTTTAATATCATTATTAATATTATTATATTCCTTTTCATCATTAATATTGCATTCAGAA

AAATGTTGTATAGTATCATCTATCTTTTTTACAGAATTCATAAAAACAGATTTATAATTTTTTTT

TGACTTATCATATAATTCTTTATTTAATAAATCGAACTTGTTATTCATTTTTTCATAAATATCTT

CCACATTTTTATTTATAAGTAATTCAATATCTTTCAAAATATTTTCTTTAAATTCTTGTATATCT

TABLE 2-continued

SEQ ID NO. 21: Sequence of P. falciparum (partial sequence; Genbank, ID Z98551).

```
TCATTTATCATTTTTTTATAATTATTAATTATAATATTATCCTCCTTTTCAAAAACATCATATTT
TTTATAAATATATTCAATGTTGTCATTCATAATCTTCTTGTCCTTATCCCAATGTATATATTTTT
CATGACATTTTTTTTCTAGTAACATAAATGATTCGTTTAAAAAATATGAAATATATTACATATAA
CTTTTAATATATTGTATTAATGATTTTGCATTATATAACTTTTTTTCAGATTCGTGATTATCTAA
ATTTTGTATAATATCTTCACCTTGTCTATTTAATAATAAATCTTTTATAAATTCTTTATTCTCAG
GATAATTAAATGATTCCTCTATATGGTCAAATGGCATCTCATTATTTTCTTCTTTACCATATTGT
TTTTGACATGTTTTTCCTTCACCATTTTGTTTTTCACATATTATTCCTTCACCGTTTTGTTTTTC
ACATATTATCTCGTCACCGTTTTGTTTTTCACATATTATCTTTTCACCACTTTGTTTTTCACATA
TTATCTCTTCACCGTTTTGTTTTTCACATATTATCTTTTCACCACTTTGTTTTTCACATATTATC
TTTTCACCACTTTGTTTTTCACATATTATCTTTTCACCACTTTGTTTTTCTTTTTTTAATCCGTT
TGTATTATATACACCAATAATTGCTGGCATTTTCTGCTTGGCTTCATCACTTATATGTGGTATGT
TTATTTTACATTGTGATATTTCCTTTTTAATATTTTCGGAGAGAGAAAAGTAATCATGATCATAT
TTTTGTAAAATATCCATATGGTCCAGTATAAAATTCAGAGTATCATTATATTTAAAATTAATGTT
ACTATTGAGTTCTTCAAAATGGTTAATATAATCATTGTATGATTTTTATTTTGTACTAGATAAT
TTTTGGTATCATCTAAAATGAATAAGATGGTTTTACATATATCGTTTAAAAGATGATTTTCTTGA
TGAATATTTTTTTTATATTTAATAGATTATCATGCATTATATTAGACATATTTGTTTTAATTTG
TTGAAAAGATTTTTTTTGATTTATAAAATTTTCTTCTAAAGAATGATATTTATTTAATAAGAATT
GTGTAATATATTTTCTTCTATTATTTTTTAATTAATATTTGATGAAATGCTTGTATATTTTA
TATTTTTGAATAGTATCTTTTAAAAAGAAAAATATTTTATTTTGTAGATCATCTGTATTATCCAT
TTTATTTAATAAATTTTTTATTTTTTACTTTTTTCAAATAAAATTTTTTCTTTTTCTAATAATA
TTTCTTTATTTTTCTTTAGACTATTTTGTATATTATTATATTCTTCTGTATCAAGATAAACACCT
CTCTTTTCTCTGCTTAAATTCAGTGCATTTCTTAACTTTTCGATTTCATTATTTAAATCCTTTAT
TTTTAATTGTTTCGTTGTTTTATATTTATCTCGGGTCTATTCTTAATATTCTTAGCTCGAAAGA
CATAATCTAAAGTGCTTAAAGTCTCATCAATACATAAAGAGGAGGGTGATATAGTGGCGACAATA
AAAGTCTTCGTTTTCCCACCTAACGAATCTTGTAATAATCTGGTTAATTTAGAATCTCTGTAAGG
AATATAAGATGAATTCTCAATCAACGAATTAATAACTCTACCTAAqGTTAATAAAGATTGATTTA
TATTACAACTTTCTTGTTGTCTAATTTTTAAAGAACCATAAGAGCTTTTCAAAGCATTTTCACTA
CCCGCTAAATCAACTAAATTTAATTTTCCTATTTTTGTTATACTTTCTCCTACATTATTTATATC
TTTTATAATTAATGTTATAGTAAAAATCGAATGACTTCTACTCGATTTTTTATTATAAGCCGTTT
CAGCTGTCCTTCTTTTTTTAATAGCTGAACATATAATATAATATATTTCTTCAAAAGAATTAATA
CTTTTTTCTTCTAACTTATCAACATTTAATCCTTTACTTTTATTATTACTATCTTCATATATTCG
AAGTTTCATATTTTCATTTGTTGAACTTAATAAATCACATAATTCTTCATTATATATTTCTAGAT
AGCTAATTTTTATATTAAAATCGTACATATTCTTATCATCAAATGTTTGATACATATCATTATTC
CTATTTTATCTACACTACATTTTTGTACAACATCACAAGTAATATCTCTACTCTTTTCGTTAAC
TAACAAATTGTTAGGTTCTTTATTAATTTTTAAATTATTATAAATATCATTTTTATOAATATTTA
TTTTGTTACATAATAAATTATTATAATTATTATTAATAATATTATTATTGTTACCATTAGTTTCC
TTATTTATTACATTTATATGTTCGTTATCCTTTTCATCAAATATATTCTTTTTCCTTTAAAATG
TCGAATCTTTTCTTCTTTCCTTTTATTTAATATATCGAATATTCTTTTCGTAACTCGAAATATAA
```

TABLE 2-continued

SEQ ID NO. 21: Sequence of P. falciparum (partial sequence; Genbank, ID Z98551).

```
GTCCAGTATCCTCATTCTCACAAAGTTCATAGCAATAGCTGATGTCGCTATTAATACTTTCATTC

AAATCCACCTTTTTATTATTATCATATTGTTTCAGGTGTTCTAGTATTTTCCCTTCCATAGTATA

GGTCTTACCCGTCCCGGTCTGTCCATAGCAGAACAGCGTACAATTGAATCCTTGCAAAACCTGAA

GCGGCGAACAAAAAAAAAAAAAAAAAAAA7TATATATATATATGTACATGTATATTTATATGTAT

ATGTATATATATATGTATAGTTATATGTATTTTTATTTTTATTTTTATTTTTATATTTATTTTA

TTTTTATATTTATTTTTATTTTTATATTTATTTTTATTTTTATATTTATATTTATATATGTGTAA

AATTAACATGGGGAGCAAAGAATTTCCCATATATTTTTTTTTTAATCTATTTAATAAAACATT

ATTATGATATACGCAGAGGTGATATATACATGGTATTTATTTATTTTTTTTATATATTTTTCAT

TTGTTTCGTAGGAATATTCTTTTTTTTTCTGCACATATATTTCACTATCCATATAATATCATAAT

ACATCATGGAATAATTTATATATATATATATATATGTATATTTTATTTTTACCTCATCTACTA

TTTGGTAAATATAATTATTGAACAAAGTTTTCTGATCCACATCTTTATCACATGCATAATCAAAA

CTATATTTTTTTCGTATATTTCATTGTTTCTATTAATTGTTAATATAACCTCATTATTATTAAT

TQGAACTACCTCTTCATTATTTATATCGTTTTTTTCTTTTTCATTTAATGGTCTACACCTTACGA

TAACTTTTATATTTACGCAACTTGATTTATCATTATTATAAGAATTTCTGAGCATTTTACTTTTA

TTCAAATAAT
```

TABLE 3

Sequence homology: Comparison of human eg5 sequence with *Plasmodium falciparum*-eg5 sequence

```
               1                                                          60
human.SEQ      GAATTCCGTCAT.........GGCGTC....GCAGCC.AAATTC...GTCTGCGAAGAAG
PLASMO.SEQ     TTTTTTTTTTTTTATTCCTTGGATGTTCTTGGTAGTTTAAATTTTTTATTTTTGTAGTTT 61                                                         120
human.SEQ      .........AAAGA....GGAGAAGGGGAAGAACATCCAGGTGGTGGTGAGATGCAGACC
PLASMO.SEQ     TCTTCTTTTATACGTTTTAAAGCACGGGATGCCTTTTTAGGAAATGCCCTATTTTCAATA 121                              45                        180
human.SEQ      A.TTTAATTTGGCAGAGCGGAAAGCTAGCGCCCAT.TCAATAGTAGAATGTGATCCTGTA
PLASMO.SEQ     GCTTTAATTTTTGTAGATTGAAATTTATTATTATTATTATTATTGT.TGTTGTTGTT 181                                                        240
human.SEQ      CGAAAAGAAGTTAGTGT.ACGAACTGGAGGATTGGCTG..ACAAGAGCTCAAGGAAAACA
PLASMO.SEQ     GTTGTTGTTGTTGTTGTTATTATTTCAATAATTATTTGTTATATGAACATTTTGAACATT 241                                                        300
human.SEQ      TACACTTTTGAT.........ATGGTGTTTGGAGC..........ATCTACTAAAC..AG
PLASMO.SEQ     TATATTTCTCTTTCTTTCATATTCTTTTAAACTTGTTACACTCATATTTTCTGTATTTAC 301                                                        360
human.SEQ      ATTGA..TGTTTACCG....AAGTGTTGTTTG.....TCCAATTCTGGATGAAGTT.AT.
PLASMO.SEQ     ATCAAATCTTTTATTATGTTGATTGTTATTTAAATAATTTAATTCTTGATATGTTTCATC 361                              60                        420
human.SEQ      TATGGGCTATA....ATTGCAC....TATCTTTGC.GTATGGC.CAAACT........GG
PLASMO.SEQ     TATTGGTTGTATAGGATTATCCGTTGTATTCTTATTATATAGCATATATTCATTTAAGGG 421                                                        480
human.SEQ      CA.....CTG.GAAAAACTTTTACAATGGA...AGGTGAAAGGTC......ACCTA....
PLASMO.SEQ     TAGATTATTCTGATTAGTTTTTACATTTAATTTATTTTTATCACCTTTATTATTTATATT
```

We claim:

1. An oligonucleotide or a derivative thereof, comprising up to 100 nucleotides, wherein the sequence of the oligonucleotide or derivative thereof comprises at least one of SEQ ID NO:1, SEQ ID NO:2, SEQ ID NO:3, SEQ ID NO:4, SEQ ID NO;5, SEQ ID NO:6, SEQ ID NO:7. SEQ ID NO:8, or SEQ ID NO:9.

2. The oligonucleotide or derivative thereof as claimed in claim 1, wherein the oligonucleotide sequence is SEQ ID NO:1, SEQ ID NO:2, SEQ ID NO:3, SEQ ID NO:4, SEQ ID NO:5, SEO ID NO:6, SEQ ID NO:7. SEQ ID NO:8, or SEQ ID NO:9.

3. The oligonucleotide or derivative thereof as claimed in claim 1, wherein the oligonucleotide or derivative thereof has one or more modifications.

4. The oligonucleotide or derivative thereof as claimed in claim 3, wherein said one or more modifications are located at one or more phosphodiester internucleoside bridges, and/or at one or more βD-2'-deoxyribose units, and/or at one or more nucleoside bases.

5. The oligonucleotide or derivative thereof as claimed in claim 3, wherein from 1 to 5 terminal nucleotides at the 5'-end and/or at the 3'-end of the oligonucleotide or derivative thereof have modified internucleoside bridges located at the 5'-end and/or the 3'-end of the nucleotide.

6. The oligonucleotide or derivative thereof as claimed in claim 3, wherein at least one internal pyrimidine nucleoside and/or an internucleoside bridge located at the 5'-end and/or the 3'-end of said at least one internal pyrimidine nucleoside is modified.

7. The oligonucleotide or derivative thereof as claimed in claim 3, wherein each modification is independently selected from:

(a) replacement of a phosphodiester bridge at a 3'- and/or a 5'-end of a nucleoside by a modified internucleoside bridge;

(b) replacement of a phosphodiester bridge at a 3'- and/or a 5'-end of a nucleoside by a dephospho bridge;

(c) replacement of a sugar phosphate residue from a sugar phosphate backbone by another residue;

(d) replacement of a βD-2'-deoxyribose unit by a modified sugar unit;

(e) replacement of a natural nucleoside base by a modified nucleoside base;

(f) conjugation to a molecule which modifies one or more properties of the oligonucleotide or derivative thereof selected from ability to penetrate a cell membrane, ability to enter a cell, stability toward nucleases, affinity for an eg5 encoding target sequence, pharmakokinetics, ability to cleave the eg5 encoding target sequence, and ability to crosslink;

(g) conjugation to a 2'-5'-linked oligoadenylate molecule or a derivative thereof, optionally via an appropriate linker molecule; and (h) introduction of a 3'-3' and/or a 5'-5' inversion at a 3'- and/or a 5'-end of the oligonucleotide or derivative thereof.

8. A method of making the oligonucteotide or derivative thereof as claimed in claim 1, comprising the step of condensing suitably protected monomers on a solid phase.

9. A method of inhibiting eg5 gene expression, comprising the step of contacting the oligonucleotide or derivative thereof as claimed in claim 1 with a nucleic acid sequence encoding an eg5 protein, wherein said oligonucleoude or derivative thereof binds with said nucleic acid sequence.

10. A pharmaceutical composition comprising at least one oligonucleotide or derivative thereof as claimed in claims 1 or 3.

11. A method of making a pharmaceutical composition comprising mixing one or more oligonucleotides or derivatives thereof as claimed in claim 1 with a physiologically acceptable excipient.

12. The method of making a pharmaceutical composition as claimed in claim 11, wherein the composition further comprises an auxiliary substance or additive.

* * * * *

UNITED STATES PATENT AND TRADEMARK OFFICE
CERTIFICATE OF CORRECTION

PATENT NO.   : 6,472,521 B1  Page 1 of 1
DATED         : October 29, 2002
INVENTOR(S)  : Eugen Uhlmann et al.

It is certified that error appears in the above-identified patent and that said Letters Patent is hereby corrected as shown below:

Column 39,
Line 45, "SEQ ID NO;5," should read -- SEQ ID NO:5, --.
Lines 45 and 50, "SEQ ID NO:7." should read -- SEQ ID NO:7, --.
Line 50, "SEO ID NO:6," should read -- SEQ ID NO:6, --.
Line 57, "βD-2'-deoxyribose" should read -- β-D-2'-deoxyribose --.

Column 40,
Line 51, "βD-2'-deoxyribose" should read -- β-D-2'-deoxyribose --.

Column 41,
Line 1, "oligonucteotide" should read -- oligonucleotide --.
Line 7, "oligonucleoude" should read -- oligonucleotide --.

Signed and Sealed this

Eighteenth Day of March, 2003

JAMES E. ROGAN
*Director of the United States Patent and Trademark Office*